United States Patent
Sabes et al.

(10) Patent No.: US 11,817,214 B1
(45) Date of Patent: Nov. 14, 2023

(54) MACHINE LEARNING MODEL TRAINED TO DETERMINE A BIOCHEMICAL STATE AND/OR MEDICAL CONDITION USING DNA EPIGENETIC DATA

(71) Applicant: Life Epigenetics, Inc., Minneapolis, MN (US)

(72) Inventors: Jon Sabes, Minneapolis, MN (US); Brian H. Chen, Minneapolis, MN (US); Randal S. Olson, Minneapolis, MN (US)

(73) Assignee: FOXO Labs Inc., Minneapolis, MN (US)

(*) Notice: Subject to any disclaimer, the term of this patent is extended or adjusted under 35 U.S.C. 154(b) by 962 days.

(21) Appl. No.: 16/579,818

(22) Filed: Sep. 23, 2019

(51) Int. Cl.
| | |
|---|---|
| G06K 9/00 | (2018.01) |
| G16H 50/20 | (2018.01) |
| G06N 20/00 | (2019.01) |
| G06Q 40/08 | (2012.01) |
| G16B 20/00 | (2019.01) |
| G16B 40/30 | (2019.01) |
| G16B 5/00 | (2019.01) |
| G16B 40/20 | (2019.01) |

(52) U.S. Cl.
CPC ............. *G16H 50/20* (2018.01); *G06N 20/00* (2019.01); *G06Q 40/08* (2013.01); *G16B 5/00* (2019.02); *G16B 20/00* (2019.02); *G16B 40/20* (2019.02); *G16B 40/30* (2019.02)

(58) Field of Classification Search
CPC ......... G16H 50/20; G06N 20/00; G06Q 40/08; G16B 5/00; G16B 20/00; G16B 40/20; G16B 40/30
See application file for complete search history.

(56) References Cited

U.S. PATENT DOCUMENTS

| | | |
|---|---|---|
| 6,566,061 B1 | 5/2003 | Philibert et al. |
| 8,637,652 B2 | 1/2014 | Philibert et al. |
| 9,273,358 B2 | 3/2016 | Philibert et al. |
| 9,994,904 B2 | 6/2018 | Philibert et al. |
| 2007/0248576 A1 | 10/2007 | Philibert et al. |
| 2007/0292880 A1 | 12/2007 | Philibert et al. |

(Continued)

FOREIGN PATENT DOCUMENTS

| | | |
|---|---|---|
| WO | 2017214397 A1 | 12/2017 |
| WO | 2018027228 A1 | 2/2018 |

OTHER PUBLICATIONS

Boodhun, et al. "Risk Prediction in Life Insurance Industry using Supervised Learning Algorithms", Complex & Intelligent Systems 4.2, 2018, pp. 145-154.

Brodley, et al., "Creating and Exploiting Coverage and Diversity", Proc. AAAI-96 Workshop on Integrating Multiple Learned Models, Portland, OR. 1996, pp. 8-14.

Final Office Action dated Sep. 9, 2020 for U.S. Appl. No. 16/579,777, "A Machine Learning Model Trained to Classify Risk Using DNA Epigenetic Data", Sabes, 21 pages.

(Continued)

*Primary Examiner* — Tom Y Lu
(74) *Attorney, Agent, or Firm* — Lee & Hayes, P.C.

(57) ABSTRACT

A machine-learning (ML) model may be trained to receive, as input, epigenetic data associated with a subject and to output a continuous value and/or a classification of a biochemical state and/or medical condition associated with a subject. For example, the biochemical state and/or medical condition may comprise an indication that the subject consumes alcohol and/or nicotine and/or that the subject is diabetic or is likely to become diabetic, to give a small non-limiting example. The epigenetic data may be derived from saliva and/or blood in some examples.

20 Claims, 6 Drawing Sheets

(56) References Cited

U.S. PATENT DOCUMENTS

| | | | |
|---|---|---|---|
| 2009/0094065 | A1 | 4/2009 | Hyde et al. |
| 2011/0223180 | A1 | 9/2011 | Aldape et al. |
| 2011/0318735 | A1 | 12/2011 | Philibert et al. |
| 2012/0108444 | A1 | 5/2012 | Philibert et al. |
| 2012/0157324 | A1 | 6/2012 | Lizardi et al. |
| 2014/0143188 | A1 | 5/2014 | Mackey et al. |
| 2015/0193577 | A1 | 7/2015 | Xiang et al. |
| 2017/0103179 | A1 | 4/2017 | Jiao et al. |
| 2017/0132362 | A1 | 5/2017 | Skinner et al. |
| 2017/0183728 | A1 | 6/2017 | Philibert et al. |
| 2017/0306405 | A1 | 10/2017 | Philibert |
| 2017/0306408 | A1 | 10/2017 | Philibert et al. |
| 2019/0256924 | A1* | 8/2019 | Vogelstein et al. .. C12Q 1/6858 |
| 2019/0264286 | A1 | 8/2019 | Dogan et al. |
| 2019/0390280 | A1 | 12/2019 | Liu et al. |
| 2020/0005901 | A1 | 1/2020 | Cohen et al. |
| 2020/0327959 | A1* | 10/2020 | Peters et al. ........... G16B 50/30 |
| 2021/0056434 | A1 | 2/2021 | Raghunathan |
| 2021/0327538 | A1* | 10/2021 | Egilsson et al. ..... C12Q 1/6883 |

OTHER PUBLICATIONS

Holder, et al., "Machine learning for epigenetics and future medical applications", Epigenetics, 12.7, 2017, pp. 505-514.

Huang, et al., "Implementation of Classifiers for Choosing Insurance Policy Using Decision Trees: A Case Study", WSEAS Transations on Computers, Issue 10, Vol. 7, Oct. 2008, pp. 1679-1689.

Joly, et al., "Life insurance: genomic stratification and risk classification", European Journal of Human Genetics 22.5, 2014, pages 575-579.

Jordan, "A Statistical Approach to Decision Tree Modeling", Machine Learning Proceedings 1994, Morgan Kaufmann, pp. 363-370.

Office Action for U.S. Appl. No. 16/579,777, mailed on Apr. 15, 2021, Sabes, "A Machine Learning Model Trained to Classify Risk Using DNA Epigenetic Data", 28 pages.

Office Action for U.S. Appl. No. 16/579,777, mailed on May 27, 2022, Sabes, "Machine Learning Model Trained to Classify Risk Using DNA Epigenetic Data", 28 Pages.

Office Action for U.S. Appl. No. 16/579,777, mailed on Nov. 3, 2021, Sabes, "Machine Learning Model Trained to Classify Risk Using DNA Epigenetic Data", 27 Pages.

Safavian, "A Survey of Decision Tree Classifier Methodology" IEEE transactions on systmes, man, and cybernetics 21.3, 1991, pp. 660-674.

Serrano, "A friendly introduction to Recurrent Neural Networks", retrieved at <<
https://www.youtube.com/watch?v=UNmqTiOnRfg>>, 3 pgs.

Zhou, et al., "Posterior probability based ensemble strategy using optimizing decision directed acyclic graph for multi-class classification" Information Sciences 400, 2017, pp. 142-156.

Non Final Office Action dated Mar. 11, 2020 for U.S. Appl. No.16/579,777 "A Machine Learning Model Trained to Classify Risk Using DNA Epigenetic Data" Sabes, 12 pages.

* cited by examiner

MACHINE LEARNING MODEL TRAINED TO DETERMINE A BIOCHEMICAL STATE AND/OR MEDICAL CONDITION USING DNA EPIGENETIC DATA

BACKGROUND

Current methods for assessing an individual's health rely primarily on subjective reporting of an individual's health history and objective health measures that provide cross-sectional pictures of an individual's current health and life-time exposure to certain health risks. For example, assessing an individual's health and future health trajectory may be based largely on biochemical (e.g., cholesterol, triglycerides, fasting glucose) and/or biophysical measures (e.g., blood pressure, tidal volume, ejection fraction) that assess a contemporary, cross-sectional picture of the metabolic state of an individual, which fail to reflect recurrent and/or life-time risk exposures. Therefore, current measures also rely on subjective reporting and/or a large repository of additional data, such as collecting measures of a health history from the user (e.g., health history questionnaires), lifestyle assessments (e.g., food frequency, smoking, and alcohol use questionnaires), and accessing data from medical charts (e.g., ICD9 billing codes, medical diagnoses, and prescriptions). However, subjective reporting is problematic because such reporting is by its nature "subjective" and may be falsified or falsely perceived by the reporter, and lifestyle assessments, medical charts, and health history do not provide a singular objective measure of health risk and may omit decades of potential risk accumulation, leaving substantial ambiguity in health risk classification.

No quantifiable measure exists for cumulative health risk itself. In other words, there is not a singular test that gives a good indicator of overall health risk (e.g., all-cause mortality risk). To give a very limited example of just a few of the tests and indicators that may be required to start to form a conception of the health risk associated with an individual, the individual's blood pressure may be tested by a professional using a blood pressure cuff or using a specialized blood pressure measuring device, blood glucose and/or total cholesterol may be tested from blood drawn by a first professional and processed in a laboratory by a second professional or by using second and third specialized devices, and/or testing cotinine and/or drug levels in urine by yet another test and/or laboratory equipment. Once all these tests have been conducted, yet another professional may examine these numbers in hopes of determining some rough estimate of overall health risk associated with the individual, such as all-cause mortality.

Moreover, testing for objective indicators of health may be invasive (e.g., blood sample, urine sample, fecal sample), financially prohibitive (e.g., magnetic resonance imaging, genome mapping), unavailable for acquisition without professional testing (e.g., acquiring one or more biological samples and processing the biological samples may require professional assistance and/or a plurality of specialized types of laboratory equipment, e.g., tidal volume, magnetic resonance imaging, various blood/urine/fecal tests), and/or may not be a sufficient signal of cumulative health risk, taken individually.

BRIEF DESCRIPTION OF THE DRAWINGS

The detailed description is described with reference to the accompanying figures. In the figures, the left-most digit(s) of a reference number identify the figure in which the reference number first appears. The same reference numbers in different figures indicate similar or identical items.

DETAILED DESCRIPTION

Figure 1:
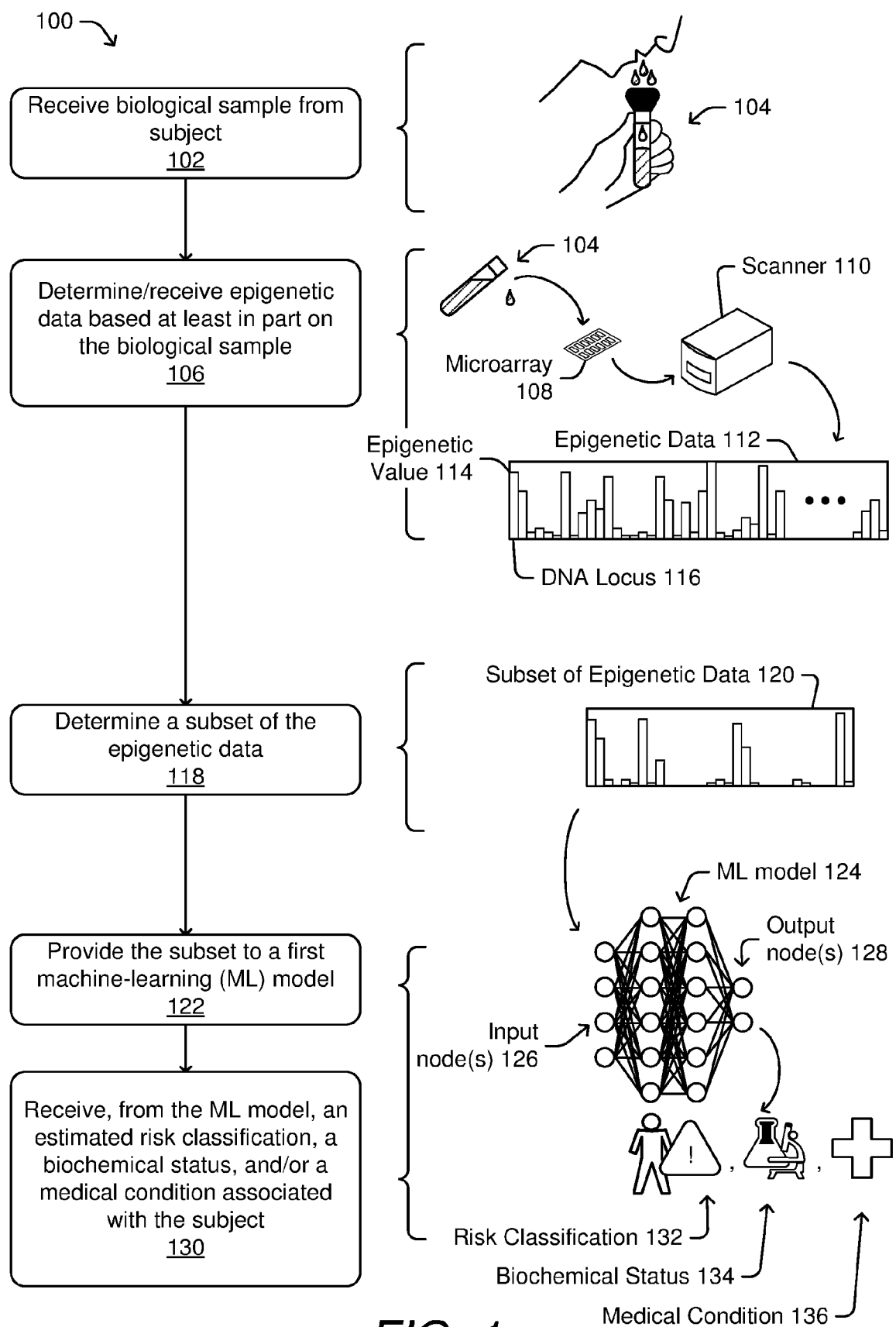
FIG. 1 illustrates a pictorial flow diagram of an example process for determining, by an ML model trained according to the techniques discussed herein, an estimated health risk classification, biochemical state, and/or medical condition using epigenetic data associated with a subject.

The techniques (e.g., machine(s) and/or process(es)) discussed herein generally relate to a machine-learning (ML) model trained to receive, as input, epigenetic data associated with a subject and to output a health risk classification associated with the subject. For the sake of example and without limitation, the health risk classification may comprise an actuarial category of risk and/or hazard ratio (e.g., hazard ratio of death or disease), although additional and alternate examples are discussed herein. Epigenetic data may comprise a measurement of methylation, acetylation, histone, and/or other similar modifications to DNA, RNA, or proteins. In some examples, the epigenetic data may be acquired from a biological sample received from the subject. The biological sample may comprise saliva and/or blood, although it is contemplated that other samples may be collected from the subject.

The techniques may comprise additional or alternate ML models trained to receive epigenetic data associated with the subject as input and to output a value associated with a biochemical state and/or a value and/or classification associated with a medical condition. For example, a value associated with a biochemical state may indicate a value associated with a level of creatinine, glucose, HDL-cholesterol, LDL-cholesterol, amphetamine, barbiturate, ketones, urobilinogen, platelet count (e.g., may include platelet distribution width), hematocrit, hemoglobin, cotinine, and/or the like. To give a non-limited example of a classification associated with a medical condition, the classification may comprise an indication of the presence or absence of alcohol use, an indication of an alcohol consumption pattern (e.g., binge drinker, consistent drinker), arrhythmia (e.g., atrial fibrillation), celiac status, dementia, diabetes (Type 1 and/or Type 2), drug abuse (e.g., illicit drug use, pharmaceutical abuse), epilepsy, hypertensive heart disease, kidney disease, liver disease, tobacco use, cannabinoid use, and/or the like. In some examples, a classification associated with a medical condition may comprise an ICD-9 code. Without limitation, examples of values associated with a medical condition may comprise a number of alcoholic drinks per time period (e.g., week, day), an alcohol consumption pattern (e.g., a number of drinks per drinking session), a number of tobacco products per time period (e.g., week, years; e.g., smoking pack-years, time since last used tobacco), a score indicating a stage of cancer, disease severity, a severity of symptomatic sensitivity, and/or the like.

In some examples, the ML model may be trained to output a confidence and/or confidence interval in association with the health risk classification, biochemical state, and/or medical condition output by the ML model. In some examples, the confidence may be a posterior probability.

The techniques discussed herein may comprise training multiple ML models using different training data sets and/or different training targets, such that different ML models may receive different inputs and/or generate different outputs. In some examples, training data sets (i.e., the observed data) for different ML models may be differentiated based at least in part on biological sample type (e.g., a first training data set may comprise first epigenetic data derived from a blood sample, a second training data set may comprise second epigenetic data derived from a saliva sample), epigenetic data type (e.g., methylation, sumoylation), an assay type by which the epigenetic data was determined (e.g., a first assay that measured DNA methylation levels at 27,578 CpG dinucleotides, such as the Illumina Infinium HumanMethylation27 BeadChip (commonly referred to as a 27k methylation array), a 450k array, an 850k array, e.g., the Illumina EPIC arraay). In an additional or alternate example, the training target, i.e., the health risk classification, biochemical state, and/or medical condition for which the ML model is trained to output an estimated epigenetic level, may be varied between different ML models. In an additional or alternate example, the ML model(s) described herein may receive additional or alternative epigenetic data as input, such as, for example, acetylation, histone protein modifications, phosphorylation, sumoylation, and/or the like.

For example, differentially training the multiple ML models may result in a first group of ML models that are all trained to output a value associated with a first medical condition, a second group of ML models that are all trained to output a classification associated with a first medical condition, a third group of ML models that are all trained to output a classification associated with a second medical condition, and so on. However, the first group of ML models may comprise a first ML model trained on DNA methylation data derived from a 27k array of DNA gathered from a saliva sample, a second ML model trained on DNA methylation data derived from a 450k array of DNA gathered from a saliva sample, a third ML model trained on DNA methylation data derived from a 27k array of DNA gathered from a blood sample, and so on. The second group of ML models may similarly include different ML models configured to receive different inputs, and so on.

In some examples, the different ML models (of a same or different group) may comprise different architectures and/or hyperparameters compared to one another. For example, training a first ML model may comprise training a plurality of ML models having different architectures and/or hyperparameters and selecting the first ML model from among the plurality of ML models based at least in part on an accuracy metric, model complexity, and/or processing speed associated with the first ML model.

In some examples, the techniques discussed herein may additionally or alternatively comprise receiving a level of coverage associated with a financial product (e.g., a level of health/life insurance coverage), an annuity amount (e.g., a pension payment, a loan where the loan is contingent on physical performance of the subject), and/or the like, and selecting at least one ML model, from among multiple ML models, based at least in part on the level of coverage, an indication of a biological sample type received in association with the subject, an assay type associated with epigenetic data associated with the subject, and/or other data associated with the subject (e.g., health history, such as medical diagnoses, self-reported data, measured biochemical states). In some examples, the other data may comprise a medical condition and/or biochemical state output by another at least one of the ML models.

In some examples, a range of coverage levels (e.g., $100,000-$200,000, although any range is contemplated) or specific level of coverage (e.g., $123,456) may be associated with a ruleset. The ruleset may specify a target criterion specifying minimum one or more data types and/or one or more thresholds associated with the one or more data types that must be satisfied for the range or specific level of coverage to be made available to the subject.

For example, a first target criterion for an m-th range of coverage levels may specify two data types, a health risk classification and biochemical state value, and thresholds associated therewith that must be satisfied (e.g., a blood pressure less than or equal to 130 mmHg, to give an example of a biochemical state value threshold; "standard non-smoker" or better for an example health risk classification threshold; "no diabetes" for an example medical condition value threshold; less than 4 drinks a week for an example medical condition value threshold). A second target criterion for determining a first medical condition may indicate a first subset of epigenetic data determined by at least a 450k array or better. A third target criterion for a second medical condition may indicate a second subset of epigenetic data.

In an additional or alternate example, the data type may indicate an array type and/or a biological sample from which epigenetic data was determined. For example, a first target criterion associated with a first range of coverage levels, $100,000-$200,000, may specify DNA methylation data determined by a 27k array as a minimum set of data (or better, such as the 450k array and/or 850k array, and/or additional data, such as a biochemical value, medical classification and/or value, etc., measured and/or inferred by an ML model), but a second target criterion associated with a second range of coverage levels, $1,000,000-$1,500,000, may specify DNA methylation data determined by an 850k array and/or a medical condition classification estimated by an ML model. If the target criterion is satisfied, a service computing device may transmit instructions to a subject's computing device instructions to make the range of coverage or the level of coverage available for selection.

In some examples, the target criterion may additionally or alternatively identify whether the data may be estimated by an ML model (e.g., an output from an ML model that indicates that the subject has diabetes) or whether it must be measured directly from a sample (e.g., fasting blood glucose test), and/or identify a threshold confidence or confidence interval associated with an output from an ML model to be acceptable for use in satisfying the target criterion. In some examples, if an estimated value or classification output by an ML model is associated with a confidence that does not satisfy the confidence threshold, the estimated value or classification cannot be used to satisfy the target criterion (e.g., which may trigger transmitting, to the subject's computing device, instructions to request additional information and/or making a range of levels of coverage unavailable for selection), but if the estimated value or classification is associated with a confidence that satisfies the confidence threshold the inferred value can be used to satisfy the target criterion.

In some examples, selecting one or more ML models, from among the plurality of ML models, may be based at least in part on the target criterion (e.g., determining outputs by the ML models that correspond to data types specified by the target criterion). Selecting the ML models may additionally or alternatively be based at least in part on an input criterion associated with an ML model, where the input criterion may identify input data type accepted by the ML model (e.g., methylation data, a subset of DNA loci associated with the ML model inputs, an assay type, a biological sample type).

In some examples, the target criterion may comprise a minimum data set required to determine instructions to transmit to the subject's computing device, wherein the instructions cause one or more levels of coverage to be available or unavailable for selection at the computing device. In some examples, the target criterion may include one or more thresholds, e.g., a threshold risk classification (e.g., an actuarial classification, an all-cause mortality indication), a threshold biochemical value, a threshold medical condition classification, and/or a threshold medical condition value. In some examples, a risk classification may be associated with a range of available levels of coverage and/or a maximum level of coverage — any levels of coverage below the maximum level of coverage may be available for selection via a user interface displayed by the subject's computing device.

The techniques discussed herein create a quantifiable measure of overall health risk and thereby improves health risk classification generally. The techniques may also reduce the number of biological samples needed from a subject to accurately determine an overall health risk associated with subject to one or two samples. In some instances, the techniques discussed herein may accurately identify a health risk classification associated with the subject using a saliva sample, which does not require any specialized personnel or devices for collection, unlike other methods which may require at least a blood sample. In another sense epigenetic data used in a machine learning model may provide a more stable estimate of a trait (e.g., average blood pressure) than a single, direct measure — equivalent to multiple, direct measures over time.

Moreover, the techniques discussed herein may provide a new way to obtain an accurate estimation of biochemical values and/or medical conditions values and/or classifications without self-reporting or more than the biological sample from which the epigenetic data is determined. For example, a saliva sample may be used to identify the existence of diabetes or alcohol use, a bilirubin level, and/or other values or classifications that may traditionally be identified using other biological samples, such as urinary, blood, other tissue, and/or fecal samples. In other words, if a urine sample is unavailable, the techniques discussed herein may be used to estimate a biochemical value and/or medical condition status and/or classification traditionally determined from a urine sample (e.g., using the ML model trained using epigenetic data discussed herein).

Additionally or alternatively, the techniques discussed herein may transform epigenetic data derived from saliva and/or blood into a risk classification, which is unconventional and not well-known or understood in the state of the art at the time of filing and represents an eligible, novel, and non-obvious transformation of DNA information.

The term, "array" or "microarray" as used herein means a tool designed to detect the presence of specific genetic sequences or alleles (some may represent methylated or unmethylated cytosines) in a plurality of genomic regions at the same time via the use of a plurality of probes that are fixed at set positions on a solid surface. The term, "probes" as used herein means a sequence of nucleic acids that have base pair complementarity to a sequence of interest. The term, "sequencing" as used herein means the process of determining a nucleic acid sequence through a variety of possible methods and technologies. The term, "synthetic probes" as used herein means probes constructed with a machine learning model designed to predict unobserved values of the target probes.

Example Operations

FIG. 1 depicts a pictorial flow diagram of an example process 100 for determining, by an ML model trained according to the techniques discussed herein, an estimated risk classification, biochemical state, and/or medical condition using epigenetic data associated with a subject. FIGS. 1-4 illustrate example processes in accordance with embodiments of the disclosure. These processes are illustrated as logical flow graphs, each operation of which represents a sequence of operations that can be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order, in parallel to implement the processes, and/or may be performed as independent processes.

At operation 102, example process 100 may comprise receiving a biological sample 104 from the subject, according to any of the techniques discussed herein. For example, the biological sample may comprise one or more samples of tissue (e.g., skin, muscle, bone, adipose tissue, microbiome) and/or one or more samples of bodily fluid (e.g., saliva, whole blood, serum, plasma). The biological sample 104 may comprise DNA and/or be selected such that the biological sample 104 is likely to comprise DNA. In some examples, DNA containing biological samples can be obtained from an individual via saliva collection, as depicted in FIG. 1, although any other method of biological sample collection may be performed, such as a blood draw.

In some examples, receiving the biological sample may additionally or alternatively comprise isolating cells of the biological sample 104 by individual cell types. For example, the different cell types may include stem cells, erythrocytes, granulocytes (e.g., neutrophils, eosinophils, basophils), agranulocytes (e.g., monocytes, lymphocytes), platelets, neurons, neuroglial cells, skeletal muscle cells, cardiac muscle cells, smooth muscle cells, chondrocytes, keratinocytes, osteoclasts, osteoblasts, melanocytes, Merkel cells, Langerhans cells, endothelial cells, epithelial cells, adipocytes, spermatozoa, ova, and/or the like.

At operation 106, example process 100 may comprise determining and/or receiving epigenetic data based at least in part on the biological sample 104, according to any of the techniques discussed herein. For example, determining the epigenetic data may comprise processing the biological sample 104 by 1) extracting genomic DNA from cells (e.g., epithelial cells, white blood cells) present in the biological sample 104 via one of several methods (e.g., salting out, phenol-chloroform, silica gel, benzyl-alcohol, magnetic beads), 2) denaturing the extracted DNA, 3) incubating the denatured DNA in a bisulfite containing compound and thermocycling at set temperatures and intervals, 4) purifying, desulphonating, and/or neutralizing of the bisulfite converted genomic DNA, and/or 5) measuring the methylation levels through DNA sequencing and/or microarray analysis. In general, this process of bisulfite sequencing differentiates and detects unmethylated versus methylated cytosines by converting unmethylated cytosine base pairs to uracil, while methylated cytosines remain. In additional or alternative examples, the DNA may not undergo bisulfite conversion and may be analyzed without alteration (steps 3-4).

In at least one example, DNA prepared according to steps 1-4 may be applied to a microarray, such as array 108, which may comprise a fluorophore-, silver-, and/or chemiluminescent-labeled probe for indicating successful/failed binding of the probe to a particular DNA locus, which may indicate that the DNA locus is methylated/unmethylated and/or a level of methylation associated with the DNA locus. For example, array 108 may comprise a microarray chip (e.g., Illumina MethylationEPIC BeadChip (850k array), IlluminaHumanMethyalation450 BeadChip (450k array), IlluminaHumanMethyalation27 BeadChip (27k array), chromatin immunoprecipitation (ChIP) microarray), a DNA chip, or a biochip. A scanner 110 may detect and quantify an intensity of the classification output (e.g., an intensity of the fluorescence associated with a probe) to determine a binary (unmethylated/methylated) or continuous (methylation level) indication of methylation at the DNA locus. In an additional or alternate example, any other method of processing the DNA may be performed (e.g., methylation specific polymerase chain reaction, methyl-sensitive cut counting, luminometric methylation assay, pyrosequencing).

Although the discussion herein discusses methylation data, it is understood that other epigenetic data such as, for example, acetylation, histone protein modifications, phosphorylation, sumoylation, and/or the like may be used to train the ML model(s) discussed herein (e.g., the ML model(s) may receive methylation data as input or any other type of epigenetic data). Epigenetic alterations to the genome comprise a host of different biochemical changes to DNA and proteins associated with it. For example, the cytosine residues of DNA may be methylated, which when methylated near regions that control gene expression (e.g., promoter regions), may alter gene expression. Another example is the modification of lysine tails on histone proteins. DNA wraps around histone proteins to form its superstructure. The modification of these tails may change the confirmation of DNA to make it more or less accessible for transcription and gene expression. These examples are not exhaustive and more are contemplated.

Regardless of what type of epigenetic data is obtained or used herein, FIG. 1 depicts an example representation of epigenetic data 112, determined by whatever means, which may comprise an epigenetic value 114 associated with a DNA locus 116. The depicted example shows additional epigenetic values associated with other DNA loci as well.

In some examples, the epigenetic values of the epigenetic data 112 may be normalized (e.g., quantile normalization, subset-quantile within array normalization (SWAN), beta-mixture quantile method, dasen, normal-exponential out-of-band (NOOB), single sample NOOB (ssNOOB)) and/or otherwise pre-processed (e.g., background correction, dye bias correction, pre-filtered to remove epigenetic values and DNA loci associated with n% of samples having detection p-values below a detection threshold, e.g., 0.05, 0.001, 0.0001, wherein n is a positive integer, e.g., 50, 30, 75). In some examples, the epigenetic value 114 may be a binary indication of methylation or unmethylation, or the epigenetic value 114 may comprise a Beta-value and/or M-value. Epigenetic "value" is also referred to herein as an epigenetic level. A Beta-value may be the ratio of the methylated probe intensity and the overall intensity (sum of methylated and unmethylated probe intensities). For example, the Beta-value for an i-th DNA locus may be defined as:

$$\beta_i = \frac{\max(y_{i,methy}, 0)}{\max(y_i, unmeth_y, 0) + \max(y_{i,methy}, 0) + \alpha} \quad (1)$$

where $y_{i,methy}$ and $y_{i,unmethy}$ are the intensities measured by the i-th methylated and unmethylated probes, respectively, and α is an offset (e.g., default value of 100) to regularize the Beta-value when the methylated and unmethylated probe intensities are low. A Beta-value of 0 indicates that all copies of the DNA locus in the sample were completely unmethylated and vice versa (full methylation of all copies of DNA locus in sample) for a Beta-value of 1.

The M-value may be the log2 ratio of the intensities of methylated probe versus unmethylated probe. For example, the M-value for an i-th DNA locus may be defines as:

$$M_i = \log_2\left(\frac{\max(y_{i,methy}, 0) + \alpha}{\max(y_{i,unmethy}, 0) + \alpha}\right) \quad (2)$$

where α is an offset (e.g., default value of 1) to decrease the sensitivity of the equation to intensity estimation errors. An M-value close to 0 indicates a similar intensity between the methylated and unmethylated probes associated with a DNA locus, which means that the DNA locus may be approximately half methylated, assuming the intensity data is normalized. A positive M-value indicates more molecules are methylated than unmethylated, whereas the opposite is true of negative M-values.

The DNA locus 116 may be related to one or more DNA base pairs. For example, a DNA locus 116 may comprise an individual DNA base pair at a particular genomic location or may be a genomic region such as a CpG island, a promoter, an enhancer, an activator, a repressor, a transcription start sites, and/or the like. While these regions are indicated, others are contemplated. For example, the DNA locus may comprise non-coding RNA molecules (nc-RNAs) such as micro RNA (miRNA), small interfering RNA (siRNA), piwi-interacting RNA (piRNA), and/or long non-coding RNA (lncRNA). These nc-RNAs may also be measured through sequencing.

At operation 118, example process 100 may comprise determining a subset 120 of the epigenetic data 112, according to any of the techniques discussed herein. For example, determining the subset of the epigenetic data 112 may be based at least in part on input accepted by an ML model and/or the particular ML model selected according to the techniques discussed herein (e.g., in regard to example process 200). In some examples, the input accepted by an ML model may be defined by an input criterion stored at a computing device that causes storage and/or execution of the ML model or is communicatively coupled to cause inputs to be provided to the ML model. For example, the input criterion may specify a subset of DNA loci and the subset 120 of the epigenetic data 112 may comprise epigenetic values associated with the subset of DNA loci.

At operation 122, example process 100 may comprise providing the subset 120 as input to an ML model 124, according to any of the techniques discussed herein. For example, the ML model 124 may comprise a classification algorithm (e.g., for an ML model that outputs a classification, such as a risk classification or a medical condition classification) or a regression algorithm (e.g., for an ML model that outputs a continuous value, such as a biochemical state value, a medical condition value, or a confidence or confidence interval). In some examples, the ML model 124 may be learned according to supervised, unsupervised, or semi-supervised learning techniques.

For example, FIG. 1 depicts the ML model 124 as a multi-layer perceptron (MLP) having an input layer comprising input node(s) 126, two hidden layers (intervening the input node(s) 126 and the output node(s) 128), and an output layer comprising output node(s) 128. In some examples, the number of input node(s) 126 may equal the number of DNA loci of the subset, and the number of output node(s) 128 may correspond to a number of outputs that the ML model 124 is trained to output. For example, the ML model 124 may be trained to output a risk classification 132, a value associated with a biochemical state 134; a classification associated with a medical condition 136, or a value associated with a medical condition 136. The ML model 124 may additionally or alternatively output a confidence score and/or confidence interval associated with the output. In at least one example, a first output node of the output node(s) 128 may output a risk classification and a second output node of the output node(s) 128 may output a confidence and/or confidence interval associated with the risk classification.

At operation 130, example process 100 may comprise receiving, from the ML model, an estimated risk classification 132, a biochemical status 134, and/or a medical condition 136 associated with the subject, according to any of the techniques discussed herein. As discussed above, the output may be indicated by a classification and/or a value. The output may additionally or alternatively comprise a confidence and/or confidence interval associated with the classification or value.

In some examples, a risk classification 132 may comprise an actuarial classification, such as a life insurance underwriting risk category (e.g., Preferred Plus Non-Nicotine, Preferred Non-Nicotine, Standard Non-Nicotine, Standard Nicotine, Uninsurable), and/or a score associated with all-cause mortality (e.g., a prognostic score, a measure of estimated time until death, a hazard ratio, mortality factor).

The techniques may comprise additional or alternate ML models trained to receive epigenetic data associated with the subject as input and to output a value associated with a biochemical state 134 and/or a value and/or classification associated with a medical condition 136. For example, a value associated with a biochemical state 134 may indicate a value associated with a level of alanine aminotransferase, albumin, alkaline phosphatase, antihepatitis B surface antigen, antibody to hepatitis C virus, apolipoprotein A1, apolipoprotein B, aspartate aminotransferase, bilirubin, total C-reactive protein, total cholesterol, CMV IgG, creatinine, cystatin C (Gentian), gamma glutamyl transferase, globulin, glucose, HDL-cholesterol, hepatitis B surface antigen, HIV antigen/antibody combination, LDL-cholesterol, probrain natriuretic peptide, N-Terminal, total prostate-specific antigen, total protein, triglycerides, urea nitrogen, calciumuric acid, very low-density lipoprotein, albumin, albumin:creatinine ratio, drug level (e.g., pharmaceutical or otherwise, amphetamine, barbiturate, benzodiazepine, cannabinoids, cocaine, opiate), ketones, leukocyte esterase, nitrite, blood/urine pH, phencyclidine, specific gravity, total protein per g creatinine ratio, urobilinogen, % basophils in blood, % eosinophils in blood, % lymphocytes in blood, %/count monocytes, %/count neutrophils, basophil count, eosinophil count, platelet count (e.g., may include platelet distribution width), hematocrit, hemoglobin, hemoglobin A1c, ion-exchange HPLC, lymphocyte count, mean corpuscular volume, mean platelet volume, red blood cell count (e.g., may include red blood cell distribution width), white blood cell count, cotinine, 4-(methylnitrosamino)-1-(3-pyridyl)-1-butanol (NNAL), carbohydrate deficient transferrin (CDT), and/or Phosphatidyl Ethanol (PEth).

To give a non-limited example of a classification associated with a medical condition 136, the classification may comprise an indication of the presence or absence of alcohol use, arrhythmia (e.g., atrial fibrillation), asthma, cardiovascular condition (e.g., angina, angioplasty or percutaneous transluminal coronary angioplasty (PTCA), percutaneous coronary intervention (PCI), coronary artery bypass graft (CABG), coronary bypass surgery, state indicative of myocardial infarction (imminent or past), congestive heart failure), cancer (e.g., bladder, brain, breast, cervical, colon and/or rectum, endometrial, esophageal, kidney and/or renal pelvis, leukemia, liver, lung and bronchus, non-Hodgkin lymphoma, oral, pancreas, prostate, skin, stomach, thyroid, uterine), celiac status, chronic obstructive pulmonary disease (COPD) (e.g., bronchitis, emphysema), cognitive impairment (e.g., mild cognitive impairment (MCI)), cerebrovascular accident (CVA) (e.g., hemorrhagic stroke, ischemic stroke, transient ischemic attack (TIA)), dementia (Alzheimer's disease, frontotemporal disorders, Lewy body dementia, vascular dementia), diabetes (Type 1 and/or Type 2), drug abuse (e.g., illicit drug use, pharmaceutical abuse), epilepsy, hypertensive heart disease (e.g., hypertension, left ventricular hypertrophy), inflammatory bowel disease (e.g., Crohn's disease, ulcerative colitis), kidney disease (e.g., chronic kidney disease, end-stage renal disease), liver disease (e.g., cirrhosis), mental illness (e.g., anxiety, bipolar, depression, post-traumatic stress disorder (PTSD)), multiple sclerosis, osteoporosis, Parkinson's disease, arthritis (e.g., rheumatoid arthritis), symptomatic sensitivity and/or an identifier of the allergen, tobacco use, and/or cannabinoid use.

Without limitation, examples of values associated with a medical condition 136 may comprise an (average) number of alcoholic drinks per time period (e.g., week, year, drinking session), an (average) number of tobacco products per time period (e.g., week, year), a score indicating a stage of cancer, disease severity, a severity of symptomatic sensitivity, and/or the like.

In some examples, the risk classification 132, biochemical state 134, and/or medical condition 136 may comprise a discriminative indication (e.g., identifying a current condition) or a forecasting indication (e.g., identifying a likelihood of a future condition).

Figure 2:
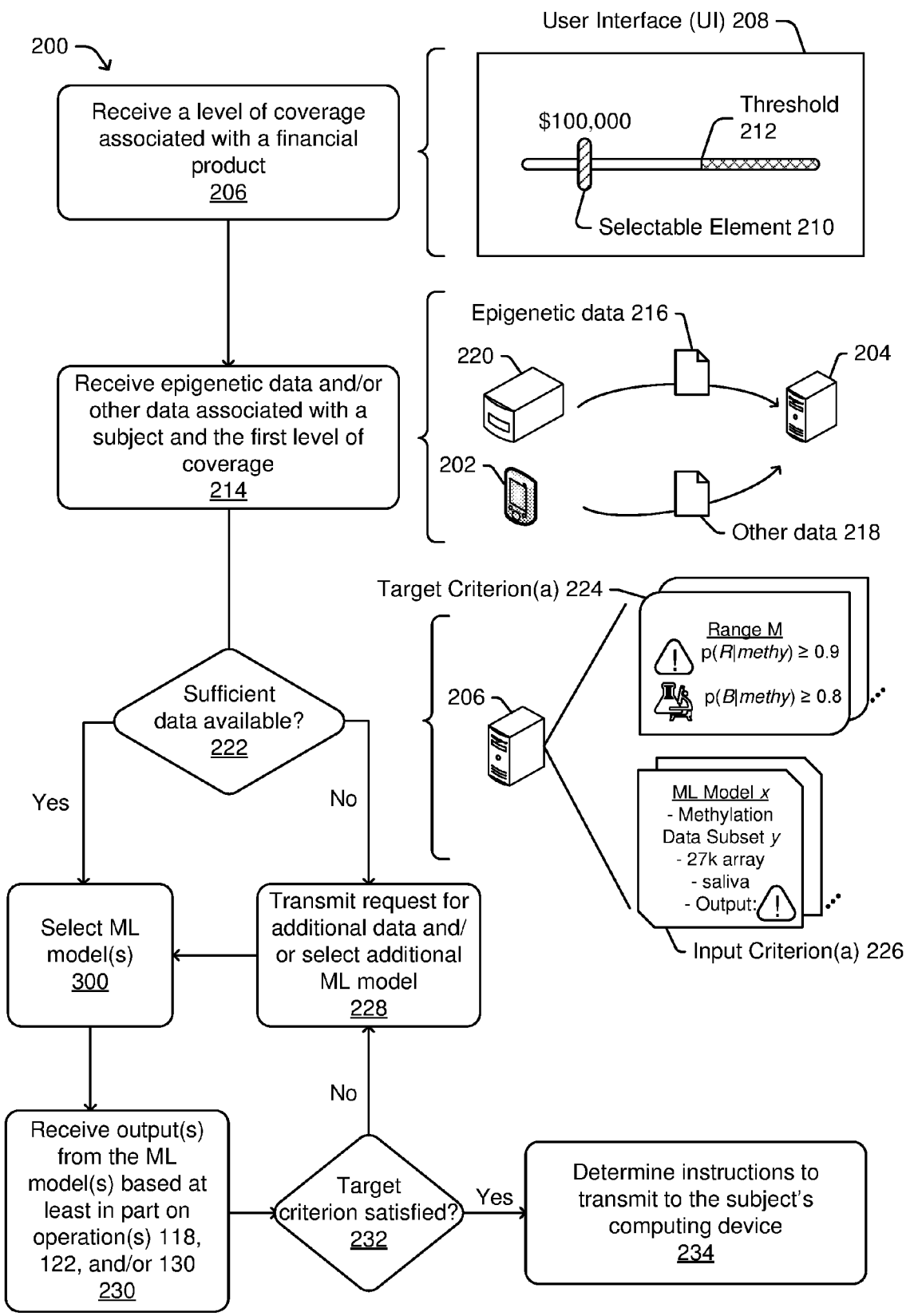
FIG. 2 illustrates a pictorial flow diagram of an example process for determining instructions to trigger a risk assessment triage testing protocol and/or to cause a range of coverage levels to be available/unavailable for selection at a subject's computing device.

FIG. 2 illustrates a pictorial flow diagram of an example process 200 for determining instructions to cause a coverage level and/or a range of coverage levels to be available/unavailable for selection at a subject's computing device 202. In some examples, the example process 200 may be used to determine one or more ML models, from among a plurality of ML models, to which to provide at least epigenetic data associated with the subject; and/or whether to determine a biochemical state and/or medical condition associated with the subject. The example process 200 may be executed or caused to be performed by a service computing device 204, although in an additional or examples, at least part of example process 200 may be performed by the subject's computing device 202.

At operation 206, example process 200 may comprise receiving a level of coverage associated with a financial product, according to any of the techniques discussed herein. For example, the level of coverage may be associated with a life expectancy or health status of the subject and may comprise a monetary amount associated with a financial product such as life insurance, health insurance, supplemental insurance, a pension, an annuity, and/or other such products. In some examples, the level of coverage may specify a specific level of coverage (e.g., a dollar amount) and/or a range of coverage levels. The level of coverage may additionally or alternatively be associated with a payment level (e.g., amount per unit of time to receive the coverage) and/or an age of the subject. In some examples, the level of coverage may be an age or another trait associated with the subject.

In some instances, the level of coverage may be a default level of coverage and/or range of coverage levels to establish a baseline available range of coverage levels for selection via a user interface (UI) 208 displayed by the subject's computing device 202. In an additional or alternate scenario, the level of coverage may be received from the subject's computing device 202, for example, responsive to manipulation of a selectable element 210 or input thereto, or any other computing device (e.g., a computing device of an insurance carrier). For example, FIG. 2 depicts the selectable element as a slider element, however the selectable element 210 may comprise a field, form field, check box, display element (e.g., hyperlinked text and/or graphics), or any other user interface element for returning a specific level or range of coverage.

In some examples, a portion of the UI 208 corresponding to one or more levels of coverage may be made available or unavailable for selection based at least in part on instructions received from the service computing device 204. For example, example process 200 may include transmitting instructions to the subject's computing device 202 based at least in part on an output of one or more ML models and/or a target criterion, as discussed in more detail below. In some examples, the instructions may identify an upper bound of a range of coverage levels or a specific level that defines a threshold 212 for levels selectable via the user interface 208. In some instances, any level of coverage below the threshold 212 may be selectable via the user interface (UI) 208 (e.g., in the depicted example, levels of coverage above the threshold 212 are indicated as being un-selectable by hashing, whereas the portion of the slider below the threshold 212 is un-hashed and selectable).

Although FIG. 2 depicts the threshold as a level of coverage, the threshold 212 may additionally or alternatively be associated with a payment level. For the sake of simplicity and without limitation, it is assumed that a payment level is held constant, although the opposite may be true and it is understood that the level of coverage and/or the payment level may vary based on each other. In other words, instead of determining a range or level of coverage that is available/ unavailable at a fixed payment level, the techniques discussed herein may additionally or alternatively include determining a payment level at a fix level or range of coverage.

At operation 214, example process 200 may comprise receiving epigenetic data 216 (or any other epigenetic data) and/or other data 218 associated with the subject, according to any of the techniques discussed herein. In some examples, the epigenetic data 216 may be received at service computing device 204, which may be communicatively coupled via a network interface to a specialized computing device 220, such as a microarray scanner or other device for determining epigenetic data from DNA. Specialized computing device 220 may determine the epigenetic data 216 and transmit the epigenetic data 216, although, in another example, the subject's computing device 202 and/or any other computing device may transmit the epigenetic data 216 to the service computing device 204.

In some examples, other data 218 may comprise self-reported data and/or medical records and may be received from the subject's computing device 202 and/or any other computing device (e.g., a computing device associated with a laboratory or physician that serviced the subject). In some examples, the other data 218 may include responses to requests for additional data, which may comprise confirmations of an estimated medical condition determined by an ML model, for example. In some examples, the service computing device 204 may store and/or execute the one or more ML models discussed herein or cause the one or more ML models to be stored and/or executed. The service computing device 204 may additionally or alternatively store the target criterion and/or input criterion discussed herein.

In some examples, the epigenetic data 216 and/or the other data 218 may be received responsive to receiving the first level of coverage or, in another example, the epigenetic data 216 and/or the other data 218 may be received independently. In some examples, example process 200 may begin with operation 214 and no level of coverage may be received (e.g., in an example where a risk classification, biochemical state, and/or medical condition associated with the subject is being determined without association to a financial product). In such an example, the service computing device 204 may receive an identification of a target, such as a risk classification, biochemical status, and/or medical condition. The epigenetic data 216 and/or other data 218 is hereafter referred to as the subject's data for simplicity.

At operation 222, example process 200 may comprise determining whether the subject's data is sufficient to determine a risk classification, biochemical state, medical condition, and/or whether to enable selection of a range and/or discrete level of coverage at the subject's computing device 202, according to any of the techniques discussed herein. Operation 222 may be based at least in part on one or more target criterion (target criterion(a) 224) and/or one or more input criterion (input criterion(a) 226) associated with one or more ML models. The target criterion(a) 224 and/or input criterion(a) 226 may be stored on or otherwise accessible to the service computing device 204.

A target criterion(a) 224 may specify a data type associated with the target (i.e., an identification of the value and/or classification that is to be determined). For example, for a target criterion(a) 224 associated with a target range of coverage levels or a specific coverage level, the data types may comprise at least a risk classification. In additional or alternate examples, the target criterion(a) 224 associated with a range of coverage levels or a specific coverage may additionally identify a biochemical state and/or a medical condition. A target criterion(a) 224 associated with a target risk classification, biochemical state, and/or medical condition may specify an epigenetic data type, a particular subset of DNA loci, a (minimum) assay type (e.g., at least a 27k array, at least a 450k array, at least an 850k array), a biological sample type (e.g., saliva, blood). In some examples, the target criterion(a) 224 may specify additional data such as, for example, an age of the subject.

In some examples, a target criterion(a) 224, regardless of the target associated therewith (e.g., range of coverage levels, specific level, risk classification) may define a data threshold associated with a data type. For example, the data threshold may comprise indicate a value and/or classification to be satisfied by the subject's data and/or an output of an ML model and/or a threshold confidence associated therewith.

In some examples, the target criterion(a) 224 associated with determining a risk classification may identify a range of coverage levels, a specific coverage level, and/or or an upper threshold of coverage associated with a specific risk classification. The target criterion(a) 224 may additionally or alternatively identify a data type that is required to determine a value and/or classification associated with a target and/or to determine whether a range of coverage levels/ level of coverage are authorized, and/or the target criterion(a) 224 may identify a data type as optional (e.g., by combinatorically weighting different input types). In some examples, the target criterion(a) 224 may identify whether a data type may be estimated by at least one ML model or whether the data type must be measured from a biological sample.

For example, a first target criterion associated with a first range of coverage levels (i.e., the range of coverage levels is the target for the first target criterion) (e.g., $1-100,000) may comprise a data structure identifying an availability of a risk classification to the service computing device 204 and a threshold risk classification (e.g., risk classifications may be associated with a hierarchy of classifications associated with an ascending amount of coverage; the first target criterion may be satisfied by a classification that matches the threshold risk classification or is better, according to the hierarchy).

A second target criterion associated with a second range of coverage levels greater that the first range of coverage levels (e.g., $1,000,000-$1,500,000) may comprise a data structure identifying:
- availability of a risk classification and a threshold risk classification (e.g., a second classification that is greater, according to the hierarchy, than the classification identified in association with the first range of coverage levels) estimated by an ML model so long as a confidence score associated risk classification meets or exceeds a first confidence threshold;
- availability of a medical condition classification associated with a smoking status of the subject, a threshold associated therewith (e.g., non-smoking), and/or an indication that this classification may be estimated by an ML model so long as a confidence score associated with this classification meets or exceeds a second threshold confidence;
- availability of a biochemical state value and/or classification associated with illicit drug use, a threshold associated therewith, and/or an indication that this classification and/or value may be estimated by an ML model so long as a confidence score associated with this classification meets or exceeds a third threshold confidence;
- availability of a measured blood pressure reading and a threshold associated therewith (e.g., 130 mmHg); and/ or the like.

A third target criterion associated with a target risk classification, biochemical state, and/or medical condition may identify an assay type, biological sample type (from which epigenetic data was determined), and/or epigenetic data type.

In some examples, in the absence of one of the data types identified by a target criterion, the target criterion may specify one or more substitute data types and/or and restrictions associated therewith (e.g., confidence and/or accuracy thresholds, thresholds associated with the values/classifications themselves, estimated or measured) that, if available, may be used to satisfy the target criterion(a) 224.

In a more specific example, Table 1 may be an example of a target criterion associated with differing levels of life insurance coverage for different ages of a subject (italicized portions indicate data types that may be estimated by an ML model discussed herein or that has components that may be estimated by an ML model discussed herein):

TABLE 1

| Amount | Ages 18-40 | Ages 41-50 | Ages 51-69 | Ages 70+ |
| --- | --- | --- | --- | --- |
| $1 - $100,000 | Urinalysis | Urinalysis | Paramed Exam | Paramed Exam |
| | Full Blood with CDT | Full Blood with CDT | Urinalysis | Urinalysis |
| | | Rx Profile | Full Blood with CDT | Full Blood with CDT |
| | | | Rx Profile | Rx Profile |
| $100,001 - $250,000 | Urinalysis | Paramed Exam | Paramed Exam | Paramed Exam |
| | Full Blood with CDT | Urinalysis | Urinalysis | Urinalysis |
| | Rx Profile | Full Blood with CDT | Full Blood with CDT | Full Blood with CDT |
| | | Rx Profile | Rx Profile | Rx Profile |
| | | | | EKG |
| $250,001 - $1,000,000 | Urinalysis | Paramed Exam | Paramed Exam | Paramed Exam |
| | Full Blood with CDT | Urinalysis | Urinalysis | Urinalysis |
| | Rx Profile | Full Blood with CDT | Blood with CDT | Full Blood with CDT |
| | | Rx Profile | Rx Profile | Rx Profile |
| | | | | Senior Supplement |
| $1,000,001 - $5,000,000 | Paramed Exam | Paramed Exam | Paramed Exam | Paramed Exam |
| | Urinalysis | Urinalysis | Urinalysis | Urinalysis |
| | Full Blood | Full Blood | Full Blood | Full Blood |
| | Rx Profile | Rx Profile | Rx Profile | Rx Profile |
| | EKG | EKG | EKG | EKG |
| | | | | Senior Supplement |
| | | | | Financial Supplement/IR |
| $5,000,001 and up | Paramed Exam | Paramed Exam | Paramed Exam | Paramed Exam |
| | Urinalysis | Urinalysis | Urinalysis | Urinalysis |
| | Full Blood | Full Blood | Full Blood | Full Blood |
| | Rx Profile | Rx Profile | Rx Profile | Rx Profile |
| | EKG | EKG | EKG | EKG |
| | Financial Supplement | Financial Supplement | Financial Supplement | Senior Supplement |
| | | | | Financial Supplement/IR |

In some examples, a target criterion may additionally or alternatively comprise thresholds associated with a target risk classification. For example, Table 2 comprises examples of three risk classifications, ordered left-to-right according to a hierarchical priority (e.g., Preferred Plus Non-Nicotine, Preferred Non-Nicotine, Standard, and indicating thresholds associated with different data types (biochemical statuses and/or medical conditions listed in the first column), wherein satisfaction of the thresholds associated with the data types may be used to enable/disable selection of a coverage level and/or determine a risk classification to output.

TABLE 2

|  | Preferred Plus Non-Nicotine | Preferred Non-Nicotine | Standard |
| --- | --- | --- | --- |
| Nicotine Use | No use of nicotine products within 60 months | No use of nicotine products within 12 months | No use of nicotine products within 12 months |
| Family History | No death or disease prior to age 60, cardiac event, or cancer of parent or sibling | No death or disease prior to age 70, cardiac event, or cancer of parent | No death, cardiac event, or cancer of parent prior to age 70 |
| Blood Pressure | 135/85 max | | 140/90 max |
| Lipids | LDL/HDL ratio ≤ 5 | LDL/HDL ratio ≤ 5.5 | LDL/HDL ratio ≤ 7 |
|  | Total Cholesterol ≤ 250 | Total Cholesterol ≤ 280 | Total Cholesterol ≤ 300 |
| Medical History | No medical conditions on blacklist. No alcohol or drug treatment within 10 years | Standard. No alcohol or drug treatment within 5 years | No |

In an additional or alternate example, at least one ML model discussed herein may determine a risk classification based at least in part on epigenetic data, without determining constituent parts, such as the biochemical statuses and/or medical conditions listed in Table 2 above. Such an ML model may receive epigenetic data as input and determine a risk classification based at least in part on the epigenetic data (e.g., Preferred Plus Non-Nicotine, Preferred Non-Nicotine).

In some examples, an individual ML model or a pipeline of ML models may be associated with an input criterion(a) 226, which may specify the type of input received by the ML model, a probability distribution associated with output of the ML model, and/or an output determined by the ML model. For example, the type of input received may comprise a subset of DNA loci for identifying epigenetic data to provide as input to the ML model, a biological sample from which epigenetic data was determine, an assay type by which the epigenetic data was determined, and/or the like.

Operation 222 may comprise determining a data set that is available to the service computing device and determining, based at least in part on a target (e.g., identification of a range of coverage levels, specific level, and/or metric, such as a risk classification, biochemical state, and/or medical condition), whether the available data meets the requirements specified by the target criterion(a) 224 and/or the input criterion(a) 226. If the data matches the requirements or provides enough information to obtain an accuracy above a threshold accuracy, the example process may transition to example process 300. Whereas, if the data is not sufficient, such as by not matching and/or including information associated with an accuracy above the threshold accuracy, example process 200 may transition to operation 228.

At operation 228, example process 200 may comprise transmitting a request for additional data and/or selecting an additional ML model, according to any of the techniques discussed herein. Transmitting a request for additional data may comprise transmitting instructions to the subject's computing device 202 to cause the UI 208 to display a questionnaire, element configured to confirm data upon selection, an element for uploading documentation, and/or the like. In at least one example, operation 228 may occur after an ML model has generated an output associated with a confidence score. If the confidence score does not satisfy a first confidence threshold (but satisfies a second confidence threshold that is lower than the second confidence threshold in some examples) operation 228 may comprise transmitting instructions to the subject's computing device 202 sufficient to allow the subject to confirm or modify an output of the ML model. In an additional or alternate example, the service computing device 204 may transmit the request to any other computing device (e.g., a medical records database, a computing device associated with a physician and/or laboratory).

Selecting an additional ML model may be based at least in part on determining that at least a portion of data specified by a target criterion(a) 224 and/or input criterion(a) 226 is unavailable to the service computing device 204 and/or determining that an output of a different ML model was insufficient to satisfy a target criterion(a) 224 (e.g., confidence score associated with the output does not satisfy a confidence threshold). The selection may comprise determining an ML model, from among a plurality of ML models, that has an output associated with the unavailable data and/or the insufficient. In some examples, an input criterion associated with the ML model may identify a data type associated with the output(s) the ML model is trained to generate. In some examples, the additional ML model may be added to a pipeline of ML models (e.g., selected at example process 300), where an output of the additional ML model may be indicated by an input criterion(a) of a second ML model selected by example process 300. Additionally or alternatively, the output of the additional ML model may be used to satisfy a rule specified by a target criterion(a) 224, and/or may be transmitted to the subject's computing device 202.

For example, service computing device 204 may have access to epigenetic data associated with a subject, but may not have access to medical records or lab results. If a biochemical status and/or medical condition is identified as at least part of a target in such an instance (e.g., a request is received identifying a biochemical state and/or medical condition, a target criterion(a) 224 identifies the biochemical state and/or medical condition, such as to determine whether to make selectable a range of coverage levels), the service computing device 204 may select ML models corresponding to the biochemical status and/or medical condition. The techniques discussed herein may include generating, by one or more ML models, a risk classification based at least in part on epigenetic data, which is useful on its own. However, in some instances, such as for high-risk subjects and/or high coverage levels, additional estimated data may be desired, such as an estimated biochemical status and/or medical condition before determining the instructions to enable/disable selection of a coverage level or range of biochemical status and/or medical condition levels.

Example process 300 may comprise selecting one or more ML models based at least in part on data type(s) identified by a target criterion(a) 224 and/or input(s) specified by input criterion(a) 226.

At operation 230, example process 200 may comprise receiving output(s) from the ML model(s), according to any of the techniques discussed herein. For example, receiving an output may be based at least in part on operations 118, 122, and/or 130 as discussed above.

At operation 232, example process 200 may comprise determining whether a target criterion is satisfied by the data available to the service computing device 204, according to any of the techniques discussed herein. Data available to the service computing device 204 may comprise output(s) of the ML model(s). In some examples, if the target criterion is not satisfied, example process 200 may transition to operation 228 (in which case, re-selection by example process 300 may or may not be necessary, depending on whether an additional ML model was selected at operation 228 that affects an output of a previously selected ML model, otherwise operation 228 may transition to operation 230 and the previously selected ML model need not be re-executed). For example, the service computing device may determine the target criterion(a) 224 is not satisfied by determining that a confidence score associated with an output does not satisfy a confidence threshold (where the output is required by the target criterion(a) 224).

In some examples, if an output fails to satisfy the target criterion(a) 224 because a confidence score associated therewith did not satisfy a confidence threshold, lower fidelity data (e.g., self-reported data, other output(s) of other ML model(s) that have a lower recall and/or accuracy associated therewith) available to the service computing device may be used to transition to operation 234. In some examples, additional data received responsive to a request transmitted at operation 228 may be used to transition to operation 234 even though a confidence score does not satisfy the confidence threshold.

If the available data satisfies the target criterion, example process 200 may transition to operation 234.

At operation 234, example process 200 may comprise determining instructions to transmit to the subject's computing device 202, according to any of the techniques discussed herein. For example, the instructions may cause the subject's computing device 202 to enable or disable selection of at least a portion of a selectable element of UI 208 corresponding to a coverage level and/or range of coverage levels (or payment level(s), as discussed above). In some examples, the instructions may be transmitted to any other device, e.g., associated with a physician, a laboratory, an insurance company, a payment provider, and/or the like. In some instances, determining the instructions may be based at least in part on the target criterion and/or data available to the service computing device 204, which may comprise output(s) of the ML model(s) received at operation 230. In some examples, determining the instructions may comprise determining a threshold 212 based at least in part on a maximum level of a range of coverage levels.

Figure 3:
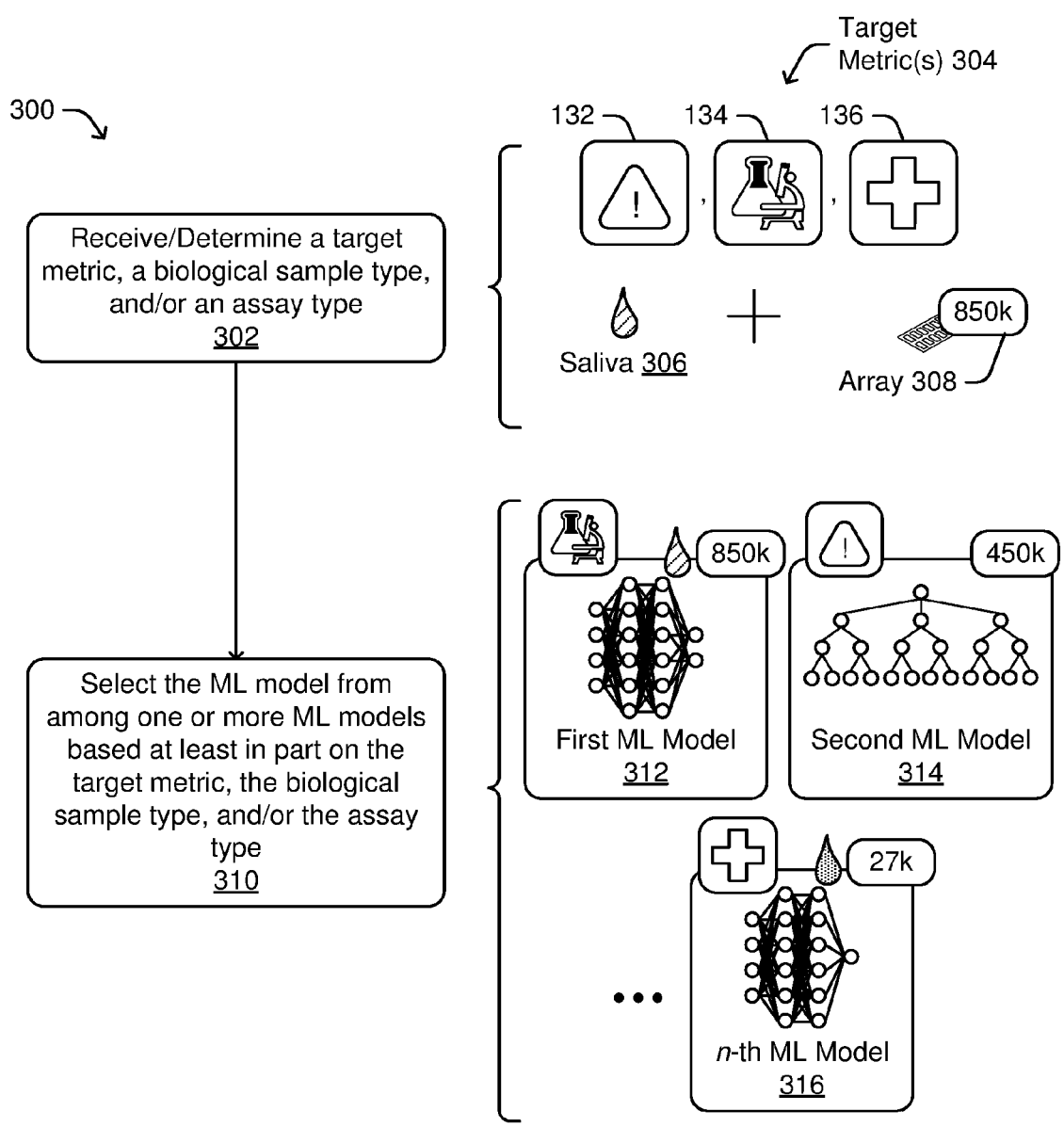
FIG. 3 illustrates a pictorial flow diagram of an example process for selecting an ML model from among multiple ML models for determining a target health risk classification, biochemical state, and/or medical condition.

FIG. 3 depicts a pictorial flow diagram of an example process 300 for selecting an ML model from among multiple ML models for determining a target risk classification, biochemical state, and/or medical condition.

At operation 302, example process 200 may comprise receiving and/or determining a target metric 304, a biological sample type, and/or an assay type, according to any of the techniques discussed herein. In some examples, the target metric may be received as part of a request received at the service computing device 204 (e.g., via a UI displayed by the service computing device 204, from another computing device, such as the subject's computing device 202 or another computing device associated with a physician, laboratory, insurance company, and/or the like). Determining the target metric may be based at least in part on determining data types required by a target criterion and/or determining data available to service computing device 204. In some examples, the target metric may comprise a risk classification 132, biochemical state 134, and/or medical condition 136.

In some examples, service computing device 204 may additionally or alternatively receive epigenetic data and/or an indication of how the epigenetic data was determined (e.g., a biological sample type, an array type). In some examples, a specialized computing device, such as a scanner, may provide the indication in a metadata file associated with the epigenetic data. FIG. 3 depicts saliva 306 as an example biological sample type and an 860k microarray 308, although any other biological sample type and/or assay type are contemplated.

At operation 310, example process 200 may comprise selecting an ML model from among one or more ML models based at least in part on the target metric, the biological sample type, and/or the assay type, according to any of the techniques discussed herein. For example, each ML model may have an input criterion associated therewith that may indicate a type of input the ML model was trained to receive and a type of output the ML model was trained to output. Operation 310 may comprise searching over the input criteria associated with the ML model(s) to determine an ML model trained to output data associated with the target metric and that receives input associated with the biological sample type and/or assay type, although, in some examples, an ML model may be trained generally (e.g., the training data used to train the ML model comprised multiple types of biological sample types and/or multiple assay types) and/or agnostically (e.g., without receiving an indication of the type of data being input). In some examples, the array type may be a minimum array type — in other words, the ML model may be trained to receive epigenetic data derived from a first array type or greater array, according to a hierarchy of arrays (e.g., 850k array provides epigenetic data for more DNA loci than a 450k array, which provides epigenetic data for more DNA loci than a 27k array; epigenetic data determined by a 850k array may be used for an ML model trained to receive 27k array epigenetic data). In some examples, the service computing device 204 may store or otherwise have access to the hierarchies discussed herein.

For example, and according to the example depicted in FIG. 3, the first ML model 312 may be trained to output a biochemical state using epigenetic data determined using a 850k array and/or a saliva sample, the second ML model 314 may be trained to output a risk classification using epigenetic data determined using a 450k array (and any sample type), and/or the n-th ML model 316 may be trained to output a medical condition using epigenetic data determined using a 24k array and/or a blood sample.

As discussed further herein, two different ML models of the plurality of ML models may be a same or different type (e.g., the first ML model 312 and the n-th ML model 316 are both depicted as being MLPs whereas the second ML model 314 is depicted as being a decision tree) and may comprise classifiers and/or regressors. ML models of a same type may have the same or different hyperparameters. Hyperparameters associated with a component of an ML model may define properties of the structure of the ML model such as, for example, a number and/or order of layers and/or nodes of the ML model, a number of nodes and/or a maximum depth of the ML model (e.g. a maximum number of child nodes in a decision tree, a maximum number of filters), a number of decision trees in a forest, a number of features considered by a tree when splitting a node, use of a Gini impurity or entropy (or gain), a dimension of filters of the layers and/or nodes, spatial extent, stride, amount of zero padding, input size (e.g., tensor, having dimensions $W_1 x H_1 x D_1$, or any other number of dimensions) and/or type (e.g., raw epigenetic data, normalized epigenetic data, tensor received from a previous component of an ML pipeline), output size and/or type (e.g., tensor having dimensions $W_1 x H_1 x D_1$ or $W_2 x H_2 x D_2$, a first dimension of a tensor indicating one or more risk classifications, one or more biochemical state values, one or more ICD-9 codes (or other medical condition indications), or one or more medical condition values; a second dimension indicating one or more confidence scores associated, respectively, with data indicated by the first dimension of the first tensor) and/or the like associated with a component of the ML model.

Although two different ML models of the plurality of ML models may have the same or similar hyperparameters, training the ML models based at least in part on different input data and/or to determine two different kinds of input may cause parameters associated with the two ML models to be different. A parameter, in contrast to a hyperparameter, may comprise any parameter that is modified during training such as, for example, a weight associated with a layer or components thereof (e.g., a filter, node). Although various examples of hyperparameters are given herein, it is contemplated that one or more of the hyperparameters may be parameters, depending on the training method.

Example Training Operations

Figure 4:
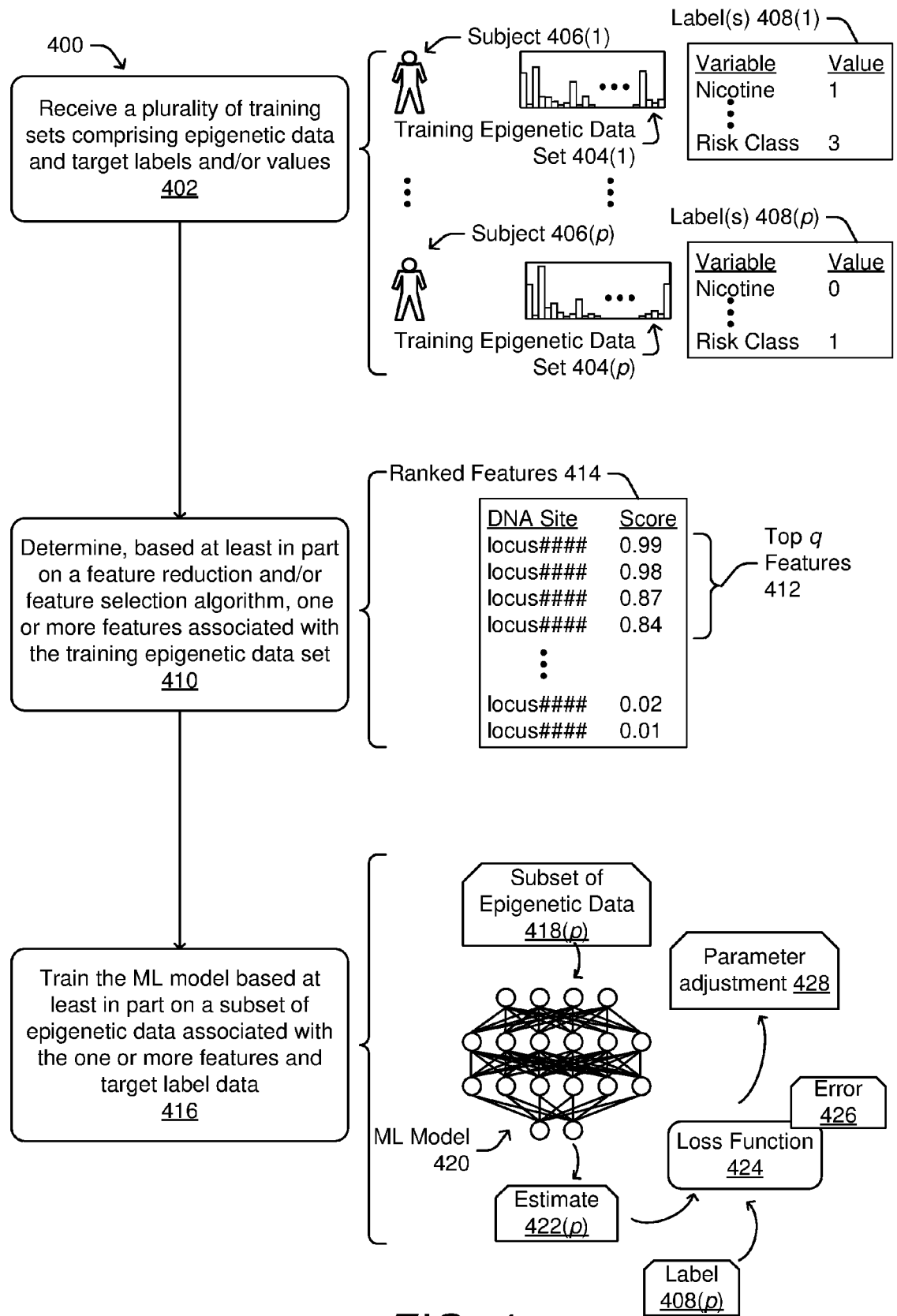
FIG. 4 illustrates a pictorial flow diagram of an example process for training at least one of the ML models discussed herein.

FIG. 4 illustrates a pictorial flow diagram of an example process for training at least one of the ML models discussed herein. The training techniques may vary based at least in part on a type and/or hyperparameters associated with ML model to be trained. In some examples, an ensemble of ML models may be trained and a best-performing ML model may be selected from among the ensemble (e.g., where best-performing may be based at least in part on an accuracy metric, model complexity, storage size, and/or speed).

At operation 402, example process 400 may comprise receiving a plurality of training sets comprising target labels and/or values, according to any of the techniques discussed herein. FIG. 4 depicts training epigenetic data sets 404(1)-(p) associated, respectively, with subjects 406(1)-(p) and label(s) 408(1)-(p), where p is a positive integer. For example, training epigenetic data set 406(p) may be determined from a biological sample received from subject 406(p) and training epigenetic data set 404(1) may be determined from a biological sample received from subject 406(1). Label(s) 408(1)-(p) may comprise ground truth data obtained from medical records, laboratory results, and/or the like. For example, label(s) 408(p) associated with the subject 406(p) may comprise one or more sets of a variable and/or value corresponding to the classifications and/or values for which an ML model is to be trained.

For example, if the ML model is to be trained to classify a subject as a nicotine user or a non-nicotine user, the label(s) 408 (p) may comprise a variable identifying the subject matter to be classified or regressed (e.g., "nicotine" in the figures) and a value associated therewith, which may comprise text (e.g., non-nicotine user, nicotine user), a code indicating a classification (e.g., 0 for no nicotine use, 1 for nicotine user; 0 for no nicotine use, 1 for former nicotine use, 2 for infrequent nicotine use, 3 for frequent nicotine use; an ICD-9 code; a code symbolizing an actuarial risk category), and/or a value (e.g., 3 {packs of cigarettes a week}, 118 {mmHg}, 102 {mg/dL}, 4 {drinks a week}). The ML model may be trained to predict multiple labels, or a single label, referred to herein as the target label(s). For simplicity we assume the ML model is being trained to predict one target label.

At operation 410, example process 400 may comprise determining, based at least in part on a feature reduction and/or feature selection algorithm, one or more features associated with the training epigenetic data set(s), according to any of the techniques discussed herein. The features selected according to operation 410 may comprise a subset of DNA loci, a biological sample type, an assay type, and/or the like, although in at least one example, the features comprise a subset of DNA loci, as FIG. 4 depicts. Operation 410 may, in some examples, select a top q features 412 from a ranked list of features 414 (where q is a positive integer), ranked according to scores determined based at least in part on a feature selection and/or feature reduction algorithm. The feature reduction and/or feature selection algorithm may comprise, for example, Spearman's rank correlation between each individual probe and the target label, retaining only the features with a non-zero coefficient from an ElasticNet model, recursive feature elimination (RFE) (e.g., repeatedly pruning a percentage of least correlated features as determined by an Extra Random Forest model that is trained on the latest subset of features until a satisfactory subset of features is achieved), principal components analysis (PCA), matrix factorization (e.g., SVD++), diversity selection based on latent space from a matrix factorization, a Relief algorithm (e.g., SURF, SURF*, MultiSURF, MultiSURF*), or a combination thereof.

In some examples, operation 410 may additionally or alternatively comprise preprocessing and/or post-processing operations, such as a second feature reduction operation (e.g., first feature reduction operation may reduce the number of DNA loci from tens of thousands to thousands, and second feature reduction operation may reduce the number of DNA loci to hundred), normalization (e.g., using quantile normalization, NOOB), scaling, smooth transformation, standardization of the data, and/or the like.

At operation 416, example process 400 may comprise training the ML model based at least in part on epigenetic values associated with a subset of the epigenetic data and/or target label data, according to any of the techniques discussed herein. Operation 416 may comprise iteratively providing training data to an ML model, receiving an estimate 422(p), and tuning the ML model based at least in part on a difference between the estimate and a label according to a supervised, or semi-supervised learning technique and/or a difference between the estimate and some indication of deviation from the observed data (e.g., an average distance to the medoid of a cluster). For example, for a p-th set of training data and/or a p-th iteration of training, operation 416 may comprise determining a subset 418(p) of the training epigenetic data set 404(p) based at least in part on the top q features determined at operation 410 (e.g., identifying the epigenetic levels associated with the q DNA loci determined as part of the top q features at operation 410). The subset 418(p) may be provided as input to the ML model 420. In some examples, the subset 418(p) may be standardized, normalized, scaled, smoothly transformed, and/or the like before being provided as input.

The ML model 420 may comprise, for example, a support vector machine (SVM) (e.g., Nystroem Kernel SVM, radial basis function (RBF) kernel SVM), a regression algorithm (e.g., ordinary least squares regression (OLSR), linear regression, logistic regression, Ridge regression, Lasso regression, ElasticNet regression), decision tree algorithms (e.g., classification and regression tree (CART), iterative dichotomiser 3 (ID3), Chi-squared automatic interaction detection (CHAID), decision stump, conditional decision trees, LightGBM, gradient-boosting machines (GBM), gradient boosted regression trees (GBRT), random forest), Bayesian algorithms (e.g., naïve Bayes, Gaussian naïve Bayes, multinomial naïve Bayes, average one-dependence estimators (AODE), Bayesian belief network (BNN), Bayesian networks), clustering algorithms (e.g., k-means, k-medians, expectation maximization (EM), hierarchical clustering), a neural network (e.g., a multilayer perceptron (MLP), ResNet50, ResNet101, ResNet 152, VGG, DenseNet, PointNet, a multi-task model that predicts multiple ones of risk classification, biochemical status(es), and/or medical condition(s), a multi-input model that receives epigenetic data associated with multiple biological sample types and/or assay types).

The ML model 420 may determine, based at least in part on the subset 418(p) and a set of parameters (e.g., a weight, bias, γ term, split points, and/or Φ term associated with a node and/or layer of the ML model 420) associated with the ML model 420, a estimate 422(p) of the target for which the ML model 420 is being trained. The estimate 422(p) may be provided to a loss function 424, which may determine an error 426 based at least in part on a difference between the estimate 422(p) and label 408(p). The loss function 424 may determine a parameter adjustment 428 to modify one or more parameters associated with the ML model 420 to minimize the error 426. For example, in an example where the ML model 420 comprises a neural network, the loss function 424 may modify the parameter(s) based at least in part on an error backpropagation technique such as, for example, a regression, gradient descent, and/or other iterative loss and determining the loss may comprise determining a cross-entropy, Huber loss, mean absolute error ("L1 loss"), mean squared error ("L2 loss"), and/or the like. In an example where the ML model 420 comprises a decision tree, the loss function 424 may comprise a cost function that determines a cost associated with a first set of split points, a minimum number of training puts per leaf, depth, number of trees, and/or ensemble selection weights and tuning the ML model 420 may comprise adjusting the split points, a minimum number of training puts per leaf, depth, etc. to minimize the cost. Tuning the parameter(s) to reduce the error 426 may increase an accuracy metric of the ML model 420 in accomplishing a task, e.g., a classification task, a regression task, and/or the like, depending on the target for which the ML model 420 is being trained.

Example Risk Classifier

Figure 5:
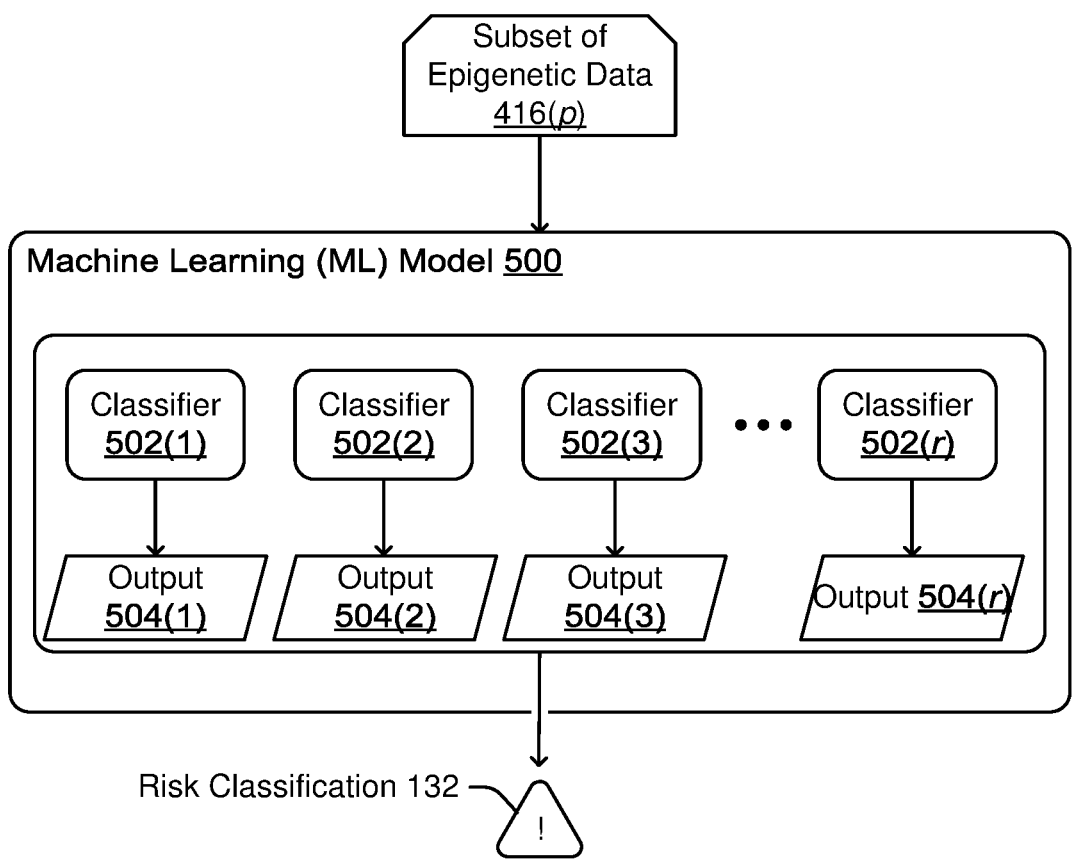
FIG. 5 illustrates a block diagram of an example ML model for health risk classification based at least in part on epigenetic data.

FIG. 5 depicts a block diagram of an example ML model 500 for risk classification based at least in part on epigenetic data. The example ML model 500 may comprise one or more classifiers (i.e., classifiers 502(1)-(r) where r is a positive integer that may correspond to a number of risk classifications). Each of the classifiers may correspond with a different risk classification, e.g., classifier 502(1) may be associated with Preferred Plus Non-Nicotine, classifier 502 (2) may be associated with Preferred Non-Nicotine, classifier 502(3) may be associated with Standard Nicotine, and so on up to the r-th risk classification. In such an example, each classifier may determine a respective output 504(1)-(r). An output 504(r) of an r-th classifier 502(r) may indicate a probability that the subject/epigenetic data is associated with an r-th risk classification associated with the classifier 502(r). In some examples, the ML model 500 may output a risk classification 132 associated with a classifier that output the maximum probability from among the outputs 504(1)-(r) (i.e., argmax technique). In an additional or alternate example, the ML model 500 may output the risk classification based at least in part on a "soft voting ensemble" technique, output blending, and/or the like. In an additional or alternate example, ML model 500 may comprise a single classifier configured to determine a risk classification to output (i.e., one model that outputs one of multiple risk classifications).

Example System

Figure 6:
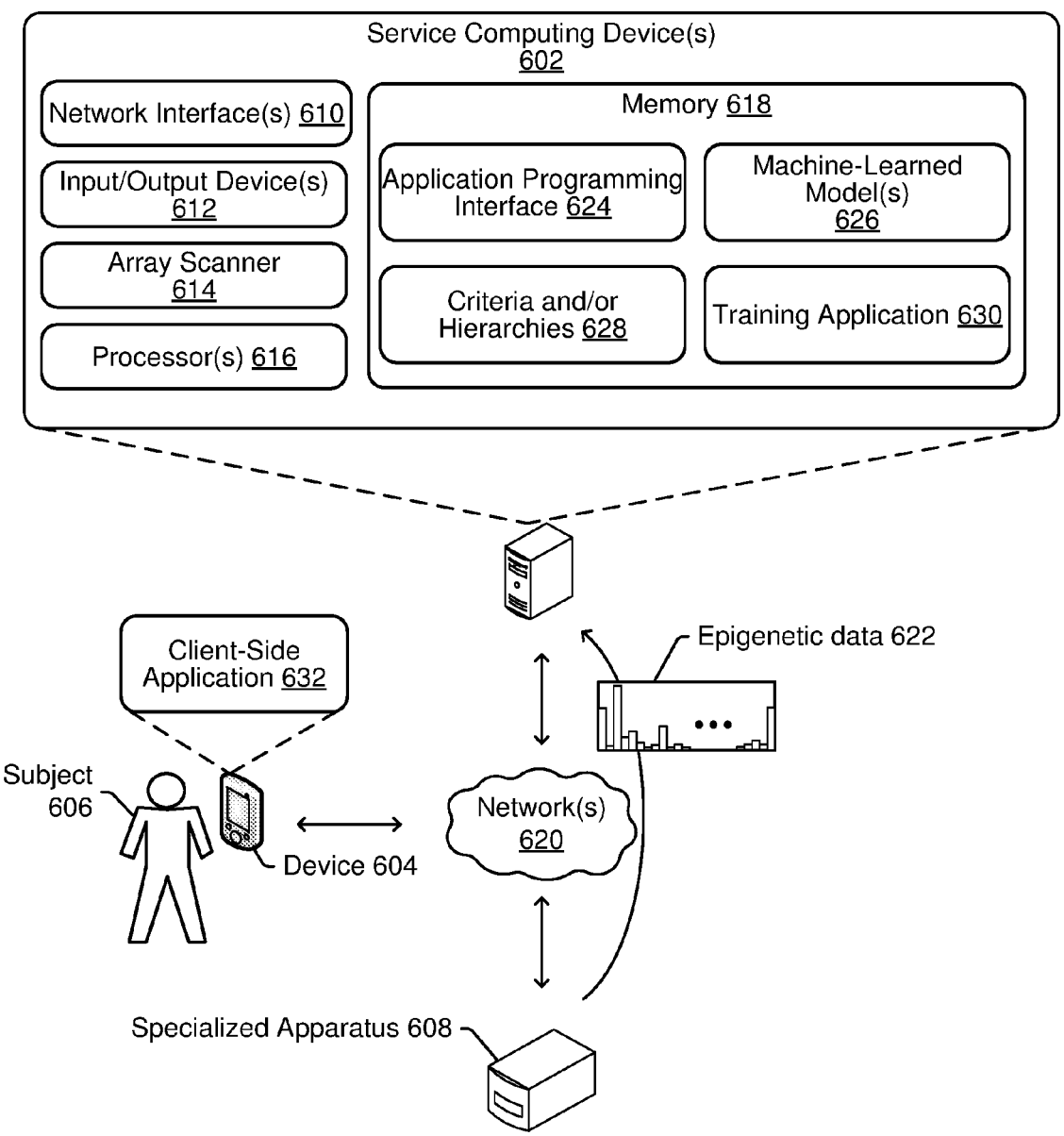
FIG. 6 illustrates a block diagram of an example system that implements the techniques discussed herein.

FIG. 6 depicts a block diagram of an example system 600 that implements the techniques discussed herein. In some instances, the system 600 may include service computing device(s) 602, which may represent service computing device 204; a device 604 associated with a subject 606, which may represent the subject's computing device 202; and a specialized apparatus 608, which may represent specialized computing device 220. In some examples, service computing device(s) 602 may comprise one or more nodes of a distributed computing system (e.g., a cloud computing architecture).

In some examples, the service computing device(s) 602 may comprise network interface(s) 610, input/output device(s) 612, an array scanner 614 (or other type of apparatus for determining epigenetic data from a DNA sample), processor(s) 616, and/or a memory 618.

Network interface(s) 610 may enable communication between the service computing device(s) 602 and one or more other local or remote computing device(s). For instance, the network interface(s) 610 may facilitate communication with other local computing device(s) of the service computing device(s). The network interface(s) 610 may additionally or alternatively enable the service computing device(s) 602 to communicate with a device 604 and/or specialized apparatus 608 via network(s) 620.

The network interface(s) 610 may include physical and/or logical interfaces for connecting the service computing device(s) 602 to another computing device or a network, such as network(s) 620. For example, the network interface(s) 610 may enable Wi-Fi-based communication such as via frequencies defined by the IEEE 802.11 standards, short range wireless frequencies such as Bluetooth®, cellular communication (e.g., 2G, 3G, 4G, 4G LTE, 5G, etc.) or any suitable wired or wireless communications protocol that enables the respective computing device to interface with the other computing device(s). In some instances, the service computing device(s) 602 may transmit instructions via the network interface(s) 610 to an application running on the device 604 to cause operations at the device 604 as discussed herein and/or transmit instructions to the specialized apparatus 608 to cause the specialized apparatus to determine epigenetic data 622 and/or transmit epigenetic data 622 to the service computing device(s) 602.

In some instances, the service computing device(s) 602 may include input/output device(s) 612 for human and/or artificial intelligence (AI) interaction with the service computing device(s) 602 (e.g., an application programming interface between an AI component and the service computing device(s) 602, keyboard, mouse, display, biometric scanner, microphone, speaker, tactile response generator).

Additionally or alternatively, the service computing device(s) 602 may comprise an array scanner 614. The array scanner 614 may represent a device similar or identical to the specialized apparatus 608 and/or may be any other component for determining epigenetic data from a DNA sample. For example, the array scanner 614 may detect fluorescent, radioactive, or other labels indicative of methylation of a DNA locus probed by a microarray.

The service computing device(s) 602 may include one or more processors, processor(s) 616, and memory 618 communicatively coupled with the processor(s) 616. The processor(s) 616 may be any suitable processor capable of executing instructions to process data and perform operations as described herein. By way of example and not limitation, the processor(s) 616 may comprise one or more central processing units (CPUs), graphics processing units (GPUs), integrated circuits (e.g., application-specific integrated circuits (ASICs), etc.), gate arrays (e.g., field-programmable gate arrays (FPGAs), etc.), and/or any other device or portion of a device that processes electronic data to transform that electronic data into other electronic data that may be stored in registers and/or memory.

Memory 618 may be an example of non-transitory computer-readable media. The memory 618 may store an operating system and one or more software applications, instructions, programs, and/or data to implement the methods described herein and the functions attributed to the various systems. In various implementations, the memory may be implemented using any suitable memory technology, such as static random access memory (SRAM), synchronous dynamic RAM (SDRAM), nonvolatile/Flash-type memory, or any other type of memory capable of storing information. The architectures, systems, and individual elements described herein may include many other logical, programmatic, and physical components, of which those shown in the accompanying figures are merely examples that are related to the discussion herein.

In some instances, the memory 618 may store an application programming interface (API) 624, ML model(s) 626, criteria and/or hierarchies 628, and/or training application 630. In some examples, the API 624 may allow the device 604 or any other device (e.g., a device associated with a physician, laboratory, insurance company, and/or the like) to transmit requests to the service computing device(s) 602, causing the service computing device(s) 602 to conduct any of the operations discussed herein, and/or to receive responses from the service computing device(s) 602, which may comprise output(s) of the machine-learned model(s) 626 and/or determinations made according to the techniques discussed herein. In some examples, the API 624 may make some of the determinations discussed herein, e.g., whether sufficient data is available to estimate a target metric, whether available data is sufficient to satisfy a target criterion, selecting ML model(s) to which to provide input data, and/or the like. In some examples, the API 624 may be based at least in part on the representational state transfer (REST) protocol, simple object access protocol (SOAP), and/or JavaScript. In some examples, the API 624 may allow computationally heavy or proprietary functions (e.g., such as the ML model(s), criteria, and/or hierarchies, and/or use thereof) to be stored remotely from users of the techniques described herein, while still providing data determined according to the techniques discussed herein to computing devices associated with the users.

For example, device 604 may execute a client-side application 632 that transmits requests to the API 624 and receives responses therefrom. In some examples, the responses may comprise the instructions discussed herein. In some examples, the client-side application may cause display of the UI discussed herein and may enable/disable selection of a coverage level and/or payment level, as discussed above.

ML model(s) 626 may include and/or represent any of the ML models discussed herein and may comprise software, hardware (e.g., a circuit configured according to parameters determined during training), or a combination thereof (e.g., an FPGA configured as an ML model). The criteria and/or hierarchies 628 may comprise a target criterion, an input criterion, and/or any of the hierarchies discussed herein (e.g., hierarchy of risk classifications, hierarchy of assays, hierarchy of biochemical states and/or medical conditions, relation between biochemical states and a medical condition). In some examples, the training application 630 may comprise software instructions for training the ML model(s) 626 (e.g., according to example process 400).

It should be noted that while FIG. 6 illustrates components of service computing device(s) 602 as being within a single system the components may alternatively be stored, executed, or exist at different systems that may be communicatively coupled. Moreover, although a component may be depicted as being part of service computing device(s) 602, alternatively, the component may be stored, executed, or exist at device 604, specialized apparatus 608, and/or any other device.

Example Clauses

A. A method comprising: receiving epigenetic data associated with a biological sample received from a subject; determining a subset of the epigenetic data based at least in part on a set of inputs accepted by a machine-learning (ML) model, the set of inputs associated with a subset of DNA loci; providing the subset of the epigenetic data to the ML model; and receiving, from the ML model, a risk classification associated with the subject.

B. The method of paragraph A, wherein: the risk classification is a first risk classification, the ML model comprises two or more classifiers, a first classifier of the two or more classifiers is associated with the first risk classification, and a second risk classifier is associated with a second risk classification.

C. The method of either paragraph A or B further comprising: receiving a first level of coverage associated with a financial product, the first level of coverage being associated with the subject; and selecting, based at least in part on the first level, the ML model from among multiple ML models, wherein the ML model is a first ML model associated with a first range of levels and a first input criteria, the first range of levels including the first level and the first input criteria specifying the set of inputs accepted by the ML model, including the subset of the epigenetic data.

D. The method of any one of paragraphs A-C, wherein selecting the ML model is further based at least in part on at least one of a biological sample type associated with the epigenetic data, an assay type by which the epigenetic data was determined, or a type of output associated with the ML model.

E. The method of any one of paragraphs A-D, further comprising: receiving, via the network interface, a second level of coverage; and selecting, based at least in part on the second level, a second ML model from among the multiple ML models, wherein: the second level is greater than the first level; the second ML model is associated with a second range of levels; and the second ML model is associated with a second input criteria associated with supplementary information associated with the subject and at least one of the subset of the epigenetic data or a second subset of the epigenetic data.

F. The method of any one of paragraphs A-E, further comprising: transmitting, to the computing device, a request for the supplementary information associated with the second input criteria; receiving, from the computing device, additional data associated with the subject; providing the additional data and at least one of the subset of the epigenetic data or a second portion of the epigenetic data to the second ML model; and receiving, from the second ML model, the risk classification or another risk classification.

G. The method of any one of paragraphs A-F, wherein the risk classification is associated with an actuarial category.

H. A system comprising: one or more processors; and a memory storing processor-executable instructions that, when executed by one or more processors, cause the system to perform operations comprising: receiving epigenetic data associated with a biological sample received from a subject; determining a subset of the epigenetic data based at least in part on a set of inputs accepted by a machine-learning (ML) model; providing at least a portion of the epigenetic data to the ML model; and receiving, from the ML model, a risk classification associated with the subject.

I. The system of paragraph H, wherein: the risk classification is a first risk classification, the ML model comprises two or more classifiers, and the first risk classification is based at least in part on a first output of a first classifier or a composite output determined based at least in part on one or more outputs of the two or more classifiers.

J. The system of either paragraph H or I, wherein the operations further comprise: receiving, via a network interface, a first level of coverage associated with a financial product; and selecting, based at least in part on the first level, the ML model from among multiple ML models, wherein the ML model is a first ML model associated with a first range of levels and a first input criteria, the first range of levels including the first level and the first input criteria specifying the set of inputs accepted by the ML model, including the subset of the epigenetic data.

K. The system of any one of paragraphs H-J, wherein the operations further comprise: receiving, via the network interface, a second level of coverage; and selecting, based at least in part on the second level, a second ML model from among the multiple ML models, wherein: the second level is greater than the first level; the second ML model is associated with a second range of levels; and the second ML model is associated with a second input criteria associated with supplementary information associated with the subject and at least one of the subset of the epigenetic data or a second subset of the epigenetic data.

L. The system of any one of paragraphs H-K, wherein the operations further comprise: transmitting, via the network interface, a request for the supplementary information associated with the second input criteria; receiving, via the network interface, additional data associated with the subject; providing the additional data and at least one of the subset of the epigenetic data or a second portion of the epigenetic data to the second ML model; and receiving, from the second ML model, the risk classification or another risk classification.

M. The system of any one of paragraphs H-L, wherein the risk classification is associated with an actuarial category.

N. A non-transitory computer-readable medium storing computer-executable instructions that, when executed by one or more processors, cause the one or more processors to perform operations comprising: receiving epigenetic data associated with a biological sample received from a subject; determining a subset of the epigenetic data based at least in part on a set of inputs accepted by a machine-learning (ML) model; providing at least a portion of the epigenetic data to the ML model; and receiving, from the ML model, a risk classification associated with the subject.

O. The non-transitory computer-readable medium of paragraph N, wherein the risk classification is a first risk classification, the ML model comprises two or more classifiers, and the first risk classification is based at least in part on a first output of a first classifier or a composite output determined based at least in part on one or more outputs of the two or more classifiers.

P. The non-transitory computer-readable medium of either paragraph N or O, wherein the operations further comprise: receiving, via a network interface, a first level of coverage associated with a financial product; and selecting, based at least in part on the first level, the ML model from among multiple ML models, wherein the ML model is a first ML model associated with a first range of levels and a first input criteria, the first range of levels including the first level and the first input criteria specifying the set of inputs accepted by the ML model, including the subset of the epigenetic data.

Q. The non-transitory computer-readable medium of paragraph P, wherein selecting the ML model is further based at least in part on at least one of a biological sample type associated with the epigenetic data, an assay type by which the epigenetic data was determined, or a type of output associated with the ML model.

R. The non-transitory computer-readable medium of any one of paragraphs N-Q, wherein the operations further comprise: receiving, from the computing device, a second level of coverage; and selecting, based at least in part on the second level, a second ML model from among the multiple ML models, wherein: the second level is greater than the first level; the second ML model is associated with a second range of levels; and the second ML model is associated with a second input criteria associated with supplementary information associated with the subject and at least one of the subset of the epigenetic data or a second subset of the epigenetic data.

S. The non-transitory computer-readable medium of any one of paragraphs N-R, wherein the operations further comprise: transmitting, to the computing device, a request for the supplementary information associated with the second input criteria; receiving, from the computing device, additional data associated with the subject; providing the additional data and at least one of the subset of the epigenetic data or a second portion of the epigenetic data to the second ML model; and receiving, from the second ML model, the risk classification or another risk classification.

T. The non-transitory computer-readable medium of any one of paragraphs N-S, wherein the risk classification is associated with an actuarial category.

U. A method comprising: training a machine-learning (ML) model to estimate a biochemical state or a medical condition associated with a first subject based at least in part on epigenetic data associated with a biological sample received from the first subject, wherein the training comprises: receiving a plurality of training sets of epigenetic data associated with different subjects, the epigenetic data being associated with a plurality of DNA loci; receiving a plurality of labels associated with the plurality of training sets, wherein a first label of the plurality of labels is associated with a second subject and comprises a classification or value associated with the biochemical state or the medical condition; determining, based at least in part on a feature reduction algorithm, a subset of DNA loci from among the plurality of DNA loci; and training the ML model based at least in part on providing, to the ML model as input, a portion of the plurality of training sets of epigenetic data corresponding to the subset of DNA loci; and determining a parameter of the ML model based at least in part on an output of the ML model and at least one of the one or more label values, wherein the output is based at least in part on the first training epigenetic values.

V. The method of paragraph U, further comprising: receiving the epigenetic data associated with the first subject; providing, as input to the ML model, a portion of the epigenetic data corresponding to the subset of DNA loci; and receiving, from the ML model, at least one of a first estimate of the biochemical state or a second estimate of the medical condition.

W. The method of paragraph U or V, further comprising: providing, as input to a second ML model, the portion or a second portion of the epigenetic data and at least one of the first estimate or the second estimate; and receiving, from the second ML model, an actuarial risk category associated with the subject.

X. The method of any one of paragraphs U-W, further comprising: receiving additional data comprising at least one of: health data associated with the subject; an age of the subject; motor vehicle records associated with the subject; a credit score associated with the subject; an occupation associated with the subject; other data associated with human health or mortality; and additionally providing the additional data to the second ML model.

Y. The method of any one of paragraphs U-X, wherein the health data may comprise at least one of: an adverse health event; a biochemical marker associated with the adverse health event; a biochemical marker associated with a disease state or process; a medical diagnosis; or a health history associated with the subject.

Z. The method of any one of paragraphs U-Y, wherein training the ML model comprises a regression technique and the biochemical state comprises at least one of a result of a blood or urine biomarker test, an average blood glucose level, average blood pressure level, average ketone level, or average hormone level.

AA. The method of any one of paragraphs U-Z, wherein training the ML model comprises a regression technique and the medical condition comprises at least one of: an estimated number of tobacco products used by the first subject within a predefined period; an estimated number of alcoholic drinks consumed by the first subject with the predefined period; or an estimated alcohol consumption pattern indicating an average number of drinks per drinking session.

AB. The method of any one of paragraphs U-AA, wherein training the ML model comprises a classification technique and the medical condition comprises at least one of an indication that the first subject: has an immune disorder; has degraded or failed organ function; has an anxiety disorder; has cancer; is diabetic; is prehypertensive or hypertensive; is depressed or has been depressed with a period of time; uses a pharmaceutical drug; uses an illicit drug; uses tobacco; or uses alcohol.

AC. A system comprising: one or more processors; and a memory storing processor-executable instructions that, when executed by the one or more processors, cause the system to perform operations comprising: training a machine-learning (ML) model to estimate a biochemical state or a medical condition associated with a first subject based at least in part on epigenetic data associated with a biological sample received from the first subject, wherein the training comprises: receiving a plurality of training sets of epigenetic data associated with different subjects, the epigenetic data being associated with a plurality of DNA loci; receiving a plurality of labels associated with the plurality of training sets, wherein a first label of the plurality of labels is associated with a second subject and comprises a classification or value associated with the biochemical state or the medical condition; determining, based at least in part on a feature reduction algorithm, a subset of DNA loci from among the plurality of DNA loci; and training the ML model based at least in part on providing, to the ML model as input, a portion of the plurality of training sets of epigenetic data corresponding to the subset of DNA loci; and determining a parameter of the ML model based at least in part on an output of the ML model and at least one of the one or more label values, wherein the output is based at least in part on the first training epigenetic values.

AD. The system of paragraph AC, wherein the operations further comprise: receiving the epigenetic data associated with the first subject; providing, as input to the ML model, a portion of the epigenetic data corresponding to the subset of DNA loci; and receiving, from the ML model, at least one of a first estimate of the biochemical state or a second estimate of the medical condition.

AE. The system of either paragraph AC or AD, wherein the operations further comprise: providing, as input to a second ML model, the portion or a second portion of the epigenetic data and at least one of the first estimate or the second estimate; and receiving, from the second ML model, an actuarial risk category associated with the subject.

AF. The system of any one of paragraphs AC-AE, wherein training the ML model comprises a regression technique and the medical condition comprises at least one of: an estimated number of tobacco products used by the first subject within a predefined period; an estimated number of alcoholic drinks consumed by the first subject with the predefined period; or an estimated alcohol consumption pattern indicating an average number of drinks per drinking session.

AG. The system of any one of paragraphs AC-AF, wherein training the ML model comprises a classification technique and the medical condition comprises at least one of an indication that the first subject: has an immune disorder; has degraded or failed organ function; has an anxiety disorder; has cancer; is diabetic; is prehypertensive or hypertensive; is depressed or has been depressed with a period of time; uses a pharmaceutical drug; uses an illicit drug; uses tobacco; or uses alcohol.

AH. A non-transitory computer-readable medium comprising computer-executable instructions that, when executed by one or more processors, cause the one or more processors to perform operations comprising: receiving a plurality of training sets of epigenetic data associated with different subjects, the epigenetic data being associated with a plurality of DNA loci; receiving a plurality of labels associated with the plurality of training sets, wherein a first label of the plurality of labels is associated with a second subject and comprises a classification or value associated with the biochemical state or the medical condition; determining, based at least in part on a feature reduction algorithm, a subset of DNA loci from among the plurality of DNA loci; and training the ML model based at least in part on providing, to the ML model as input, a portion of the plurality of training sets of epigenetic data corresponding to the subset of DNA loci; and determining a parameter of the ML model based at least in part on an output of the ML model and at least one of the one or more label values, wherein the output is based at least in part on the first training epigenetic values.

AI. The non-transitory computer-readable medium of paragraph AH, wherein the operations further comprise:

receiving the epigenetic data associated with the first subject; providing, as input to the ML model, a portion of the epigenetic data corresponding to the subset of DNA loci; and receiving, from the ML model, at least one of a first estimate of the biochemical state or a second estimate of the medical condition.

AJ. The non-transitory computer-readable medium of either paragraph AH or AI, wherein the operations further comprise: providing, as input to a second ML model, the portion or a second portion of the epigenetic data and at least one of the first estimate or the second estimate; and receiving, from the second ML model, an actuarial risk category associated with the subject.

AK. The non-transitory computer-readable medium of any one of paragraphs AH-AJ, wherein training the ML model comprises a regression technique and the medical condition comprises at least one of: an estimated number of tobacco products used by the first subject within a predefined period; an estimated number of alcoholic drinks consumed by the first subject with the predefined period; or an estimated alcohol consumption pattern indicating an average number of drinks per drinking session.

AL. The non-transitory computer-readable medium of any one of paragraphs AH-AK, wherein training the ML model comprises a classification technique and the medical condition comprises at least one of an indication that the first subject: has an immune disorder; has degraded or failed organ function; has an anxiety disorder; has cancer; is diabetic; is prehypertensive or hypertensive; is depressed or has been depressed with a period of time; uses a pharmaceutical drug; uses an illicit drug; uses tobacco; or uses alcohol.

AM. The non-transitory computer-readable medium of any one of paragraphs AH-AL, wherein the operations further comprise: receiving a first level of coverage associated with a financial product, the first level of coverage being associated with the subject; and selecting, based at least in part on the first level, the ML model from among multiple ML models, wherein the ML model is a first ML model associated with a first range of levels and a first input criteria, the first range of levels including the first level and the first input criteria specifying the set of inputs accepted by the ML model, including the subset of the epigenetic data.

AN. The non-transitory computer-readable medium of any one of paragraphs AH-AM, wherein the operations further comprise: providing, as input to a second ML model, the portion or a second portion of the epigenetic data and at least one of the first estimate or the second estimate; and receiving, from the second ML model, an actuarial risk category associated with the subject.

While the example clauses described above are described with respect to one particular implementation, it should be understood that, in the context of this document, the content of the example clauses can also be implemented via a method, device, system, computer-readable medium, and/or another implementation. Additionally, any of examples A-AN may be implemented alone or in combination with any other one or more of the examples A-AN.

Conclusion

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

The components described herein represent instructions that may be stored in any type of computer-readable medium and may be implemented in software and/or hardware. All of the methods and processes described above may be embodied in, and fully automated via, software code components and/or computer-executable instructions executed by one or more computers or processors, hardware, or some combination thereof. Some or all of the methods may alternatively be embodied in specialized computer hardware.

Conditional language such as, among others, "may," "could," "may" or "might," unless specifically stated otherwise, are understood within the context to present that certain examples include, while other examples do not include, certain features, elements and/or steps. Thus, such conditional language is not generally intended to imply that certain features, elements and/or steps are in any way required for one or more examples or that one or more examples necessarily include logic for deciding, with or without user input or prompting, whether certain features, elements and/or steps are included or are to be performed in any particular example.

Conjunctive language such as the phrase "at least one of X, Y or Z," unless specifically stated otherwise, is to be understood to present that an item, term, etc. may be either X, Y, or Z, or any combination thereof, including multiples of each element. Unless explicitly described as singular, "a" means singular and plural.

Any routine descriptions, elements or blocks in the flow diagrams described herein and/or depicted in the attached figures should be understood as potentially representing modules, segments, or portions of code that include one or more computer-executable instructions for implementing specific logical functions or elements in the routine. Alternate implementations are included within the scope of the examples described herein in which elements or functions may be deleted, or executed out of order from that shown or discussed, including substantially synchronously, in reverse order, with additional operations, or omitting operations, depending on the functionality involved as would be understood by those skilled in the art.

In the description of examples, reference is made to the accompanying drawings that form a part hereof, which show by way of illustration specific examples of the claimed subject matter. It is to be understood that other examples can be used and that changes or alterations, such as structural changes, can be made. Such examples, changes or alterations are not necessarily departures from the scope with respect to the intended claimed subject matter. While the steps herein can be presented in a certain order, in some cases the ordering can be changed so that certain inputs are provided at different times or in a different order without changing the function of the systems and methods described. The disclosed procedures could also be executed in different orders. Additionally, various computations that are herein need not be performed in the order disclosed, and other examples using alternative orderings of the computations could be readily implemented. In addition to being reordered, the computations could also be decomposed into sub-computations with the same results.

What is claimed is:
1. A method comprising:

training a machine-learning (ML) model to estimate a biochemical state or a medical condition associated with a first subject based at least in part on epigenetic data associated with a biological sample received from the first subject, wherein the training comprises:
    receiving a plurality of training sets of epigenetic data associated with different subjects, the epigenetic data being associated with a plurality of DNA loci;
    receiving a plurality of labels associated with the plurality of training sets, wherein a first label of the plurality of labels is associated with a second subject and comprises a classification or value associated with the biochemical state or the medical condition;
    determining, based at least in part on a feature reduction algorithm, a subset of DNA loci from among the plurality of DNA loci; and
    training the ML model based at least in part on:
        providing, to one or more input nodes of the ML model, a portion of the plurality of training sets of epigenetic data corresponding to the subset of DNA loci;
        determining, by one or more hidden layers based at least in part on providing the portion to the one or more input nodes, an intermediate output;
        determining, by an output layer based at least in part on the intermediate output, an output; and
        altering a parameter of the ML model based at least in part on a loss determined between the output of the ML model and at least one of the one or more label values, wherein the output is based at least in part on the first training epigenetic values.

2. The method of claim 1, further comprising:
receiving the epigenetic data associated with the first subject;
providing, as input to the ML model, a portion of the epigenetic data corresponding to the subset of DNA loci; and
receiving, from the ML model, at least one of a first estimate of the biochemical state or a second estimate of the medical condition.

3. The method of claim 2, further comprising:
providing, as input to a second ML model, the portion or a second portion of the epigenetic data and at least one of the first estimate or the second estimate; and
receiving, from the second ML model, an actuarial risk category associated with the subject.

4. The method of claim 3, further comprising:
receiving additional data comprising at least one of:
    health data associated with the subject;
    an age of the subject;
    motor vehicle records associated with the subject;
    a credit score associated with the subject;
    an occupation associated with the subject;
    other data associated with human health or mortality; and
additionally providing the additional data to the second ML model.

5. The method of claim 4, wherein the health data may comprise at least one of:
an adverse health event;
a biochemical marker associated with the adverse health event;
a biochemical marker associated with a disease state or process;
a medical diagnosis; or
a health history associated with the subject.

6. The method of claim 1, wherein training the ML model comprises a regression technique and the biochemical state comprises at least one of a result of a blood or urine biomarker test, an average blood glucose level, average blood pressure level, average ketone level, or average hormone level.

7. The method of claim 1, wherein training the ML model comprises a regression technique and the medical condition comprises at least one of:
an estimated number of tobacco products used by the first subject within a predefined period;
an estimated number of alcoholic drinks consumed by the first subject with the predefined period; or
an estimated alcohol consumption pattern indicating an average number of drinks per drinking session.

8. The method of claim 1, wherein training the ML model comprises a classification technique and the medical condition comprises at least one of an indication that the first subject:
has an immune disorder;
has degraded or failed organ function;
has an anxiety disorder;
has cancer;
is diabetic;
is prehypertensive or hypertensive;
is depressed or has been depressed with a period of time;
uses a pharmaceutical drug;
uses an illicit drug;
uses tobacco; or
uses alcohol.

9. A system comprising:
one or more processors; and
a memory storing processor-executable instructions that, when executed by the one or more processors, cause the system to perform operations comprising:
    training a machine-learning (ML) model to estimate a biochemical state or a medical condition associated with a first subject based at least in part on epigenetic data associated with a biological sample received from the first subject, wherein the training comprises:
        receiving a plurality of training sets of epigenetic data associated with different subjects, the epigenetic data being associated with a plurality of DNA loci;
        receiving a plurality of labels associated with the plurality of training sets, wherein a first label of the plurality of labels is associated with a second subject and comprises a classification or value associated with the biochemical state or the medical condition;
        determining, based at least in part on a feature reduction algorithm, a subset of DNA loci from among the plurality of DNA loci; and
        training the ML model based at least in part on:
            providing, to the ML model as input, a portion of the plurality of training sets of epigenetic data corresponding to the subset of DNA loci; and
            determining a parameter of the ML model based at least in part on an output of the ML model and at least one of the one or more label values, wherein the output is based at least in part on the first training epigenetic values; and
    receiving the epigenetic data associated with the first subject;
    providing, as input to the ML model, a portion of the epigenetic data corresponding to the subset of DNA loci;
    receiving, from the ML model, a final output indicating at least one of a first estimate of the biochemical state, a second estimate of the medical condition, or an actuarial category; and
    transmitting an instruction to a user device configured to cause the user device to limit input via a user interface to a coverage level below a maximum coverage level determined based at least in part on the final output.

10. The system of claim 9, wherein the operations further comprise:
    receiving the epigenetic data associated with the first subject;
    providing, as input to the ML model, a portion of the epigenetic data corresponding to the subset of DNA loci; and
    receiving, from the ML model, at least one of a first estimate of the biochemical state or a second estimate of the medical condition.

11. The system of claim 9, wherein the operations further comprise:
    providing, as input to a second ML model, the portion or a second portion of the epigenetic data and at least one of the first estimate or the second estimate; and
    receiving, from the second ML model, an actuarial risk category associated with the subject.

12. The system of claim 9, wherein training the ML model comprises a regression technique and the medical condition comprises at least one of:
    an estimated number of tobacco products used by the first subject within a predefined period;
    an estimated number of alcoholic drinks consumed by the first subject with the predefined period; or
    an estimated alcohol consumption pattern indicating an average number of drinks per drinking session.

13. The system of claim 9, wherein training the ML model comprises a classification technique and the medical condition comprises at least one of an indication that the first subject:
    has an immune disorder;
    has degraded or failed organ function;
    has an anxiety disorder;
    has cancer;
    is diabetic;
    is prehypertensive or hypertensive;
    is depressed or has been depressed with a period of time;
    uses a pharmaceutical drug;
    uses an illicit drug;
    uses tobacco; or
    uses alcohol.

14. A non-transitory computer-readable medium comprising computer-executable instructions that, when executed by one or more processors, cause the one or more processors to perform operations comprising:
    receiving a plurality of training sets of epigenetic data associated with different subjects, the epigenetic data being associated with a plurality of DNA loci;
    receiving a plurality of labels associated with the plurality of training sets, wherein a first label of the plurality of labels is associated with a second subject and comprises a classification or value associated with a biochemical state or a medical condition;
    determining, based at least in part on a feature reduction algorithm, a subset of DNA loci from among the plurality of DNA loci; and
    training an ML model based at least in part on:
        providing, to one or more input nodes of the ML model, a portion of the plurality of training sets of epigenetic data corresponding to the subset of DNA loci;
        determining, by one or more hidden layers based at least in part on providing the portion to the one or more input nodes, an intermediate output;
        determining, by an output layer based at least in part on the intermediate output, an output; and
        determining a parameter of the ML model based at least in part on the output of the ML model and at least one of the one or more label values, wherein the output is based at least in part on the first training epigenetic values.

15. The non-transitory computer-readable medium of claim 14, wherein the operations further comprise:
    receiving the epigenetic data associated with the first subject;
    providing, as input to the ML model, a portion of the epigenetic data corresponding to the subset of DNA loci; and
    receiving, from the ML model, at least one of a first estimate of the biochemical state or a second estimate of the medical condition.

16. The non-transitory computer-readable medium of claim 15, wherein the operations further comprise:
    providing, as input to a second ML model, the portion or a second portion of the epigenetic data and at least one of the first estimate or the second estimate; and
    receiving, from the second ML model, an actuarial risk category associated with the subject.

17. The non-transitory computer-readable medium of claim 14, wherein training the ML model comprises a regression technique and the medical condition comprises at least one of:
    an estimated number of tobacco products used by the first subject within a predefined period;
    an estimated number of alcoholic drinks consumed by the first subject with the predefined period; or
    an estimated alcohol consumption pattern indicating an average number of drinks per drinking session.

18. The non-transitory computer-readable medium of claim 14, wherein training the ML model comprises a classification technique and the medical condition comprises at least one of an indication that the first subject:
    has an immune disorder;
    has degraded or failed organ function;
    has an anxiety disorder;
    has cancer;
    is diabetic;
    is prehypertensive or hypertensive;
    is depressed or has been depressed with a period of time;
    uses a pharmaceutical drug;
    uses an illicit drug;
    uses tobacco; or
    uses alcohol.

19. The non-transitory computer-readable medium of claim 14, wherein the operations further comprise:
    receiving a first level of coverage associated with a financial product, the first level of coverage being associated with the subject; and
    selecting, based at least in part on the first level, the ML model from among multiple ML models, wherein the ML model is a first ML model associated with a first range of levels and a first input criteria, the first range of levels including the first level and the first input criteria specifying the set of inputs accepted by the ML model, including the subset of the epigenetic data.

20. The non-transitory computer-readable medium of claim 15, wherein the operations further comprise:
    providing, as input to a second ML model, the portion or a second portion of the epigenetic data and at least one of the first estimate or the second estimate; and
    receiving, from the second ML model, an actuarial risk category associated with the subject.

* * * * *